(12) United States Patent
Naota et al.

(10) Patent No.: US 9,187,510 B2
(45) Date of Patent: Nov. 17, 2015

(54) LIGHT-EMITTING ORGANIC PLATINUM COMPLEX, LIGHT-EMITTING MATERIAL CONTAINING THIS COMPLEX AND FUNCTIONAL DEVICE

(75) Inventors: Takeshi Naota, Suita (JP); Naruyoshi Komiya, Suita (JP); Minoru Okada, Suita (JP)

(73) Assignee: OSAKA UNIVERSITY, Osaka (JP)

( * ) Notice: Subject to any disclaimer, the term of this patent is extended or adjusted under 35 U.S.C. 154(b) by 648 days.

(21) Appl. No.: 13/583,153

(22) PCT Filed: Feb. 18, 2011

(86) PCT No.: PCT/JP2011/053475
§ 371 (c)(1),
(2), (4) Date: Sep. 6, 2012

(87) PCT Pub. No.: WO2011/111497
PCT Pub. Date: Sep. 15, 2011

(65) Prior Publication Data
US 2013/0001535 A1    Jan. 3, 2013

(30) Foreign Application Priority Data
Mar. 11, 2010   (JP) ................................. 2010-054699

(51) Int. Cl.
| | | |
|---|---|---|
| H01L 51/54 | (2006.01) |
| C09K 11/06 | (2006.01) |
| C07F 15/00 | (2006.01) |
| H01L 51/00 | (2006.01) |
| C07C 251/24 | (2006.01) |
| H05B 33/14 | (2006.01) |
| H01L 51/50 | (2006.01) |

(52) U.S. Cl.
CPC ........... *C07F 15/0093* (2013.01); *C07C 251/24* (2013.01); *C09K 11/06* (2013.01); *H01L 51/0087* (2013.01); *H05B 33/14* (2013.01); *C09K 2211/1007* (2013.01); *C09K 2211/1011* (2013.01); *C09K 2211/185* (2013.01); *H01L 51/5016* (2013.01)

(58) Field of Classification Search
CPC ........... H01L 51/0087; H01L 51/5016; C09K 2211/185; C09K 11/06; C07F 15/0093
See application file for complete search history.

(56) References Cited

U.S. PATENT DOCUMENTS

2009/0218938 A1*   9/2009   Takeda et al. .................. 313/504

FOREIGN PATENT DOCUMENTS

| JP | 2004-155711 | 6/2004 |
| JP | 2009-215277 | 9/2009 |
| JP | 2009-224763 | 10/2009 |
| JP | 2010-135689 | 6/2010 |

OTHER PUBLICATIONS

Shimazaki, Yuichi, et al., "Syntheses and Electronic Structures of One-Electron-Oxidized Group 10 Metal(II)-(Disalicylidene)diamine Complexes (Metal=Ni, Pd, Pt)", J. Am. Chem. Soc. (2007) vol. 129, No. 9, pp. 2559-2568.
Shimazaki, Yuichi, et al., "Detailed Evaluation of the Geometric and Electronic Structures of One-Electron Oxidized Group 10 (Ni, Pd, and Pt) Metal(II)-(Disalicylidene)diamine Complexes," Inorganic Chemistry (2009) vol. 48, No. 17, pp. 8383-8392.
Semenistaya, T.V., et al., "Synthesis of Novel Cu (II), Ni (II), Pd (II), Pt (II) Complexes and Electroconductive Photosensitive Polymers Based Theon," Russian Journal of Inorganic Chemistry (2003), vol. 48, No. 4, pp. 602-610.
Shagisultanova, G.A., et al., "Possibilities of X-Ray Photoelectron Spectroscopy Method in Studying the Structure and Properties of Polymers Based on Transition Metal Complexes with Schiff Bases," Russian Journal of Inorganic Chemistry (2005) vol. 50, No. 6, pp. 991-1004.
Yamada, Shoichiro, et al., "Palladium(II)- and Platinum(II)-complexes of Schiff Bases Derived from Salicylaldehyde and Alkylamines," Bulletin of the Chemical Society of Japan (1963) vol. 36, No. 4, pp. 483-485.
Abstract of the 59th Japan Society of Coordination Chemistry Symposium 2Ab-05, (Sep. 26, 2009).
Sun, Yinghui, et al., "Luminescent One-Dimensional Nanoscale Materials with PtII—Pt11 Interactions**", Chem. Commun. (Angew. Chem. Int. Ed) (2006), 45, pp. 5610-5613.
Abstract of the 91st Spring Meeting (Mar. 11, 2011) of the Chemical Society of Japan 1 A3-55.
Abstract of the 91st Spring Meeting (Mar. 11, 2011) of the Chemical Society of Japan, 2 A5-47.
Abstract of the 91st Spring Meeting (Mar. 11, 2011) of the Chemical Society of Japan, 2 A5-49.
Abstract of the 92nd Spring Meeting (Mar. 25, 2012) of the Chemical Society of Japan, 1 H1-57.
Abstract of the 92nd Spring Meeting (Mar. 26, 2012) of the Chemical Society of Japan, 2 K3-47.
Pacifichem 2010, 388 , abstract.
Pacifichem 2010, 389 , abstract.

* cited by examiner

*Primary Examiner* — Marie R. Yamnitzky
(74) *Attorney, Agent, or Firm* — Casimir Jones S.C.

(57) ABSTRACT

The present invention provides a light-emitting organic platinum complex, a light-emitting material containing with complex, and a functional device containing this complex. The light-emitting organic platinum complex is represented the following structural formula or other formulae as described herein.

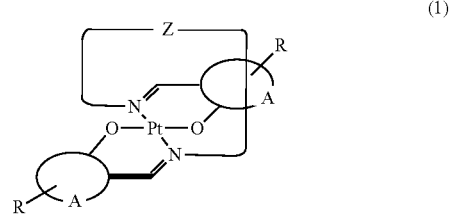

(1)

4 Claims, 1 Drawing Sheet

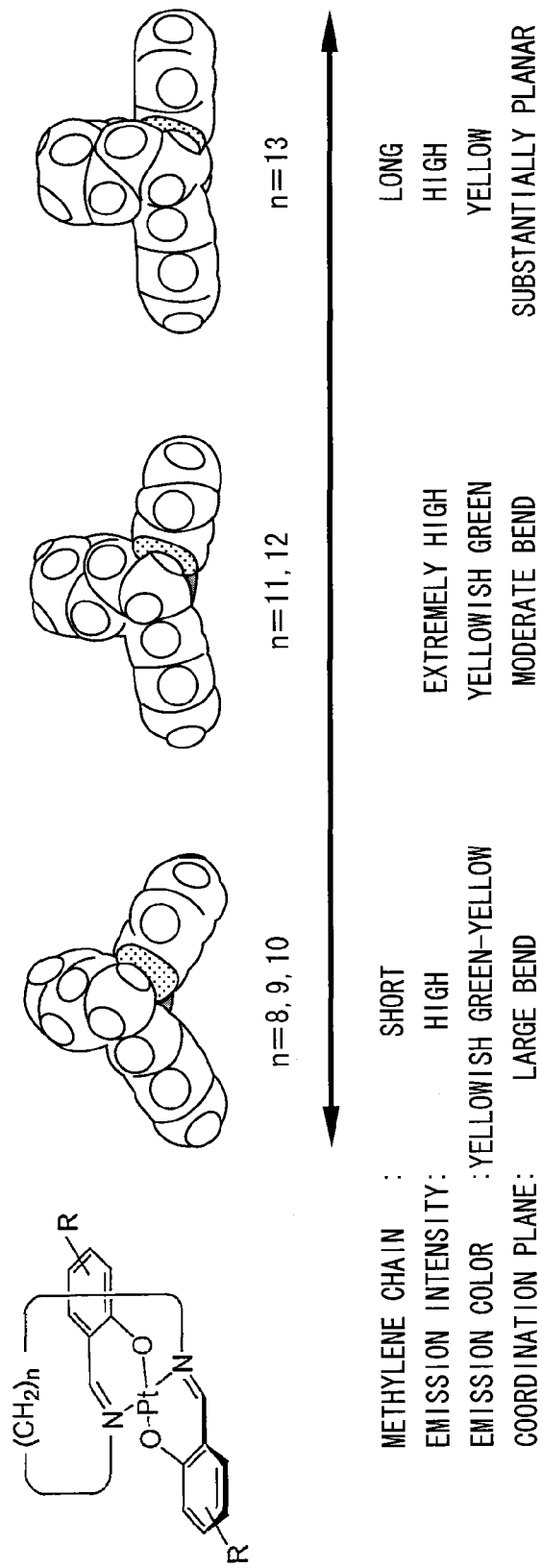

LIGHT-EMITTING ORGANIC PLATINUM COMPLEX, LIGHT-EMITTING MATERIAL CONTAINING THIS COMPLEX AND FUNCTIONAL DEVICE

TECHNICAL FIELD

The present invention relates to (i) a light-emitting organic platinum complex useful as a material for a functional device such as an organic light-emitting element, (ii) a light-emitting material including the light-emitting organic platinum complex, and (iii) a functional device.

BACKGROUND ART

An organometallic complex emits phosphorescent light that can be, in organic EL (electroluminescence), theoretically higher in quantum efficiency than fluorescent light. This makes organometallic complexes promising as a material (specifically, as a material for an organic EL display) for a functional device such as an organic light-emitting element, which represents a next-generation technique. Currently, however, there is a demand for improvement in such aspects of organometallic complexes as life, heat resistance, and efficiency achieved when there has been an increase in current. Further, an organometallic complex, in order to be used in a functional device, needs to produce all the three primary colors (red, green, and blue) of light.

Recent years have witnessed various organometallic complexes being proposed each of which is useful as a material for a functional device. Patent Literature 1, for example, discloses a metalloporphyrin complex including a metal such as platinum and having a cross-linked structure. Patent Literature 2 discloses an organometallic complex including (i) a metal such as iridium and platinum and (ii) a heterocyclic compound as a ligand.

CITATION LIST

Patent Literature 1
Japanese Patent Application Publication, Tokukai, No. 2004-155711 A (Publication Date: Jun. 3, 2004)
Patent Literature 2
Japanese Patent Application Publication, Tokukai, No. 2009-224763 A (Publication Date: Oct. 1, 2009)

SUMMARY OF INVENTION

Technical Problem

The metalloporphyrin complex disclosed in Patent Literature 1, although having a cross-linked structure, unfortunately includes as a ligand a porphyrin that keeps a planar structure. This arrangement causes the metalloporphyrin complex to (i) have a high rate of radiationless deactivation and a light-emission quantum yield φ of approximately several percent and thus to (ii) have a low luminous efficiency. This prevents the metalloporphyrin complex from achieving emission intensity sufficient for practical use. Further, the metalloporphyrin complex requires synthesis through a reaction having a large number of stages (approximately nine stages), which makes its production method complicated. In addition, the metalloporphyrin complex can only limitedly emit light having a color tone corresponding to red of a wavelength of approximately 650 nm, and thus cannot produce all the three primary colors of light. Similarly, the organometallic complex disclosed in Patent Literature 2 also (i) has a high rate of radiationless deactivation due to its molecular movement and a light-emission quantum yield φ of 15% or below, and thus (ii) has a low luminous efficiency. This prevents the organometallic complex from achieving emission intensity sufficient for practical use.

In other words, the above conventional organometallic complexes, each having a low luminous efficiency, problematically fail to (i) achieve emission intensity sufficient for practical use and (ii) produce all the three primary colors of light.

The inventors of the present invention have conducted a diligently examination to solve the above problem, and consequently found that (i) in the case where a cross-linked structure formed by a cross-linking chain such as a methylene chain has been introduced in a ligand of a light-emitting organic platinum complex, such a light-emitting organic platinum complex has increased emission intensity, which is sufficient for practical use even at room temperature (23° C.), and that (ii) adjusting the length of the above cross-linking chain can control the color tone of light emission. The inventors of the present invention have, as a result, completed the present invention.

The present invention has been accomplished in view of the above problem. It is a main object of the present invention to provide (i) a light-emitting organic platinum complex that is superior in luminous efficiency to conventional organometallic complexes, that can achieve emission intensity sufficient for practical use, that can produce all the three primary colors of light, and that is useful as a material for a functional device such as an organic light-emitting element, (ii) a light-emitting material containing the light-emitting organic platinum complex, and (iii) a functional device containing the light-emitting organic platinum complex.

Solution to Problem

In order to solve the above problem, a light-emitting organic platinum complex of the present invention is represented by any one of structural formulae below:

[Chem. 1]

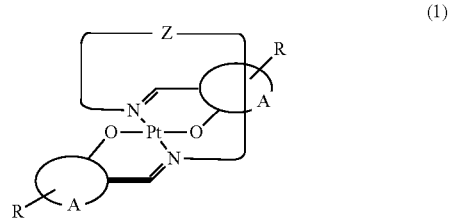

(1)

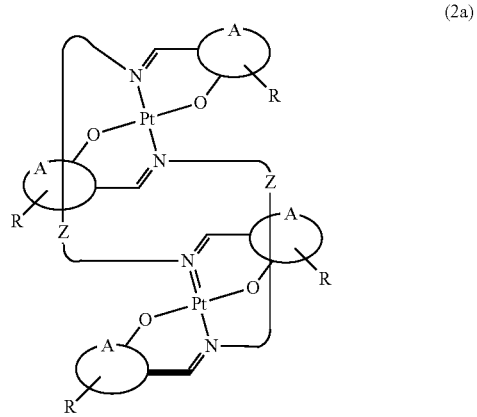

(2a)

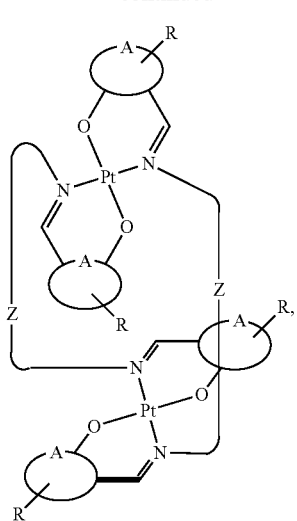

(2b)

where: Z represents either —(CH$_2$)$_n$— or —CH$_2$(CH$_2$OCH$_2$)$_m$CH$_2$—, where n represents an integer of 7 to 14, and m represents either 3 or 4; A represents either an optionally condensed aromatic hydrocarbon ring or an optionally condensed heteroaromatic ring; R is a substituent group for A and represents hydrogen (unless n of Z in the structural formula (1) is 7 to 13), a halogen, an alkyl group having 1 to 6 carbon atoms, an alkenyl group having 1 to 6 carbon atoms, an alkynyl group having 1 to 6 carbon atoms, an alkoxy group having 1 to 6 carbon atoms, a halogenated alkoxy group represented by —OC$_p$H$_q$X$_r$, a hydroxyl group, a hydroxyethyl group, an alkyl amino group represented by —NR$_1$R$_2$, a nitro group, a sulfonyl group, a sulfinyl group, a carboxyl group, an acetoxy group, a ureido group, a phenyl group, an alkyl phenyl group having 7 to 13 carbon atoms, an alkyl phenyl oxy group having 7 to 13 carbon atoms, an alkynyl phenyl group having 8 to 13 carbon atoms, an alkenyl phenyl group having 8 to 13 carbon atoms, or a phenoxy group, where X represents a halogen, p represents an integer of 1 to 6, q represents 0 or a positive integer and satisfies "2p+1=q+r", r represents a positive integer and satisfies "2p+1=q+r", and R$_1$ and R$_2$ are each independently hydrogen or an alkyl group having 1 to 6 carbon atoms, a plurality of R being optionally present in A, the plurality of R present in A being optionally different from one another.

The light-emitting organic platinum complex of the present invention may preferably be arranged such that:

(a) the light-emitting organic platinum complex is represented by the structural formula (1); Z is —(CH$_2$)$_n$—; n is an integer of 8 to 14; A is a benzene ring; and R is a halogen, a methyl group, an ethyl group, a methoxy group, an ethoxy group, a trifluoromethoxy group, a difluoromethoxy group, a hydroxyl group, a hydroxyethyl group, a dimethylamino group, a diethylamino group, a nitro group, an acetoxy group, a phenyl group, an alkyl phenyl oxy group having 7 to 13 carbon atoms, an alkynyl phenyl group having 8 to 13 carbon atoms, an alkenyl phenyl group having 8 to 13 carbon atoms, or (in a case of n=14) hydrogen;

(b) the light-emitting organic platinum complex is represented by the structural formula (2a) or (2b); Z is —(CH$_2$)$_n$—; n is an integer of 7 to 14; A is a benzene ring; and R is hydrogen, a halogen, a methyl group, an ethyl group, a methoxy group, an ethoxy group, a trifluoromethoxy group, a difluoromethoxy group, a hydroxyl group, a hydroxyethyl group, a dimethylamino group, a diethylamino group, a nitro group, an acetoxy group, a phenyl group, an alkyl phenyl oxy group having 7 to 13 carbon atoms, an alkynyl phenyl group having 8 to 13 carbon atoms, or an alkenyl phenyl group having 8 to 13 carbon atoms;

(c) the light-emitting organic platinum complex is represented by the structural formula (1); Z is —CH$_2$(CH$_2$OCH$_2$)$_m$CH$_2$—; m represents 3 or 4; A is a benzene ring; and R is hydrogen, a halogen, a methyl group, an ethyl group, a methoxy group, an ethoxy group, a trifluoromethoxy group, a difluoromethoxy group, a hydroxyl group, a hydroxyethyl group, a dimethylamino group, a diethylamino group, a nitro group, an acetoxy group, a phenyl group, an alkyl phenyl oxy group having 7 to 13 carbon atoms, an alkynyl phenyl group having 8 to 13 carbon atoms, or an alkenyl phenyl group having 8 to 13 carbon atoms; or (d) the light-emitting organic platinum complex is represented by the structural formula (2a) or (2b); Z is —CH$_2$(CH$_2$OCH$_2$)$_m$CH$_2$—; m represents 3 or 4; A is a benzene ring; and R is hydrogen, a halogen, a methyl group, an ethyl group, a methoxy group, an ethoxy group, a trifluoromethoxy group, a difluoromethoxy group, a hydroxyl group, a hydroxyethyl group, a dimethylamino group, a diethylamino group, a nitro group, an acetoxy group, a phenyl group, an alkyl phenyl oxy group having 7 to 13 carbon atoms, an alkynyl phenyl group having 8 to 13 carbon atoms, or an alkenyl phenyl group having 8 to 13 carbon atoms.

Further, in order to solve the above problem, a light-emitting organic platinum complex of the present invention is represented by any one of structural formulae below:

[Chem. 2]

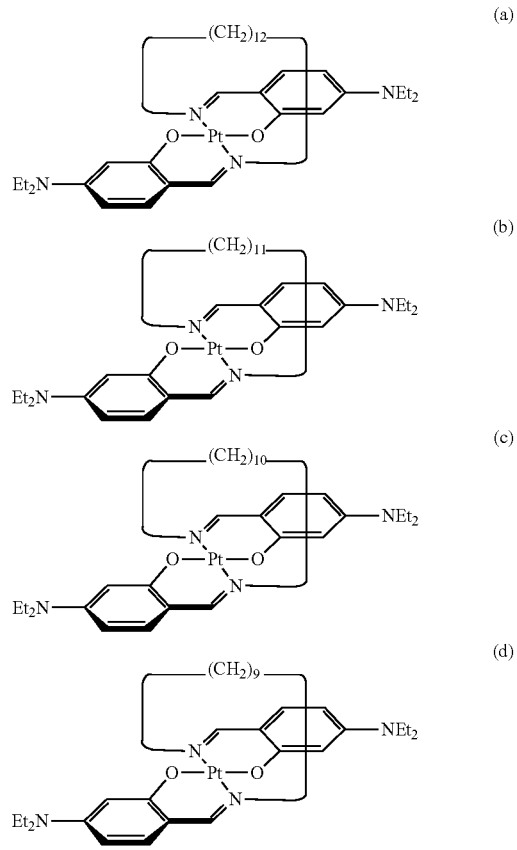

(e)
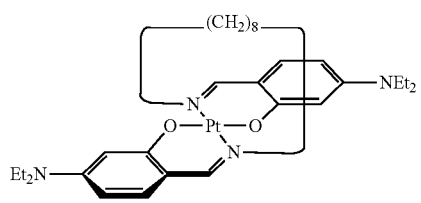
(f)
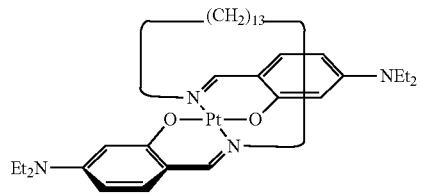
(g)
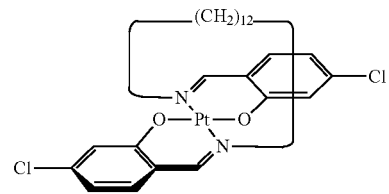
(h)
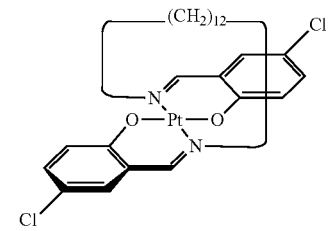
(i)
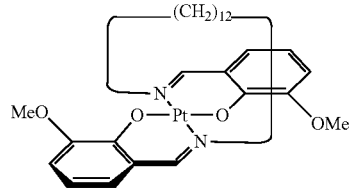
(j)
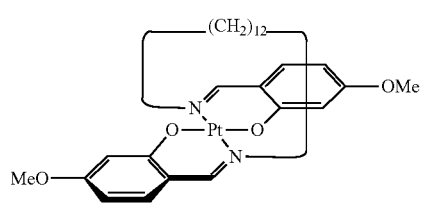
(k)
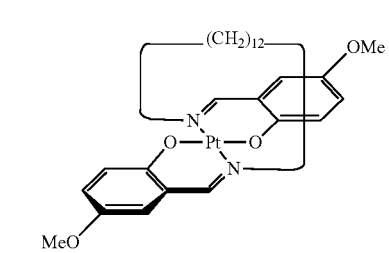
(l)
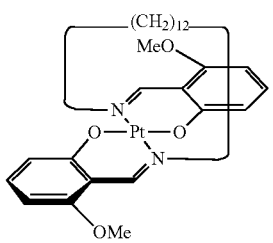
(m)
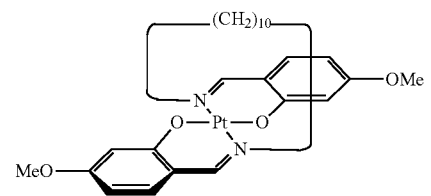
(n)
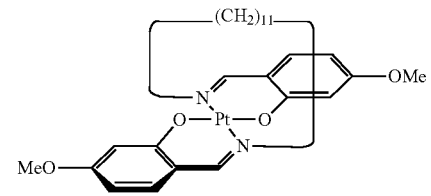
(o)
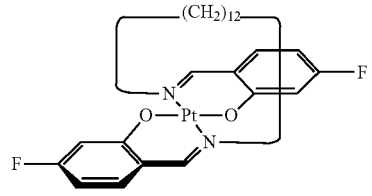
(p)
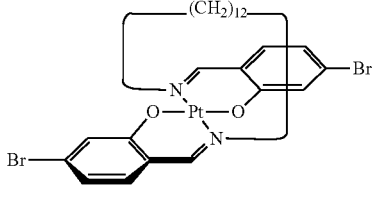
(q)
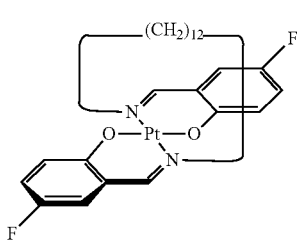
(r)
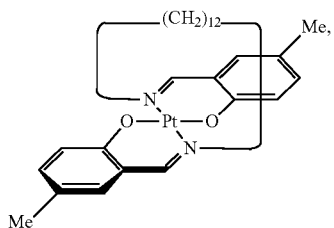

[Chem. 3]
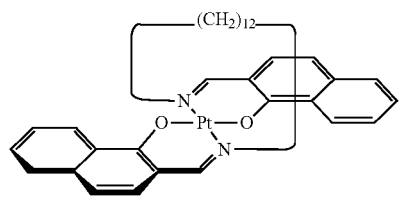 (s)
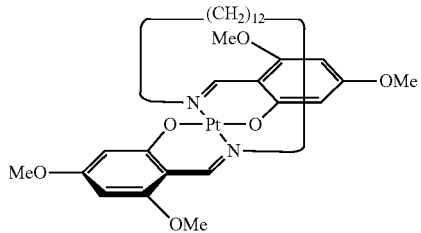 (t)
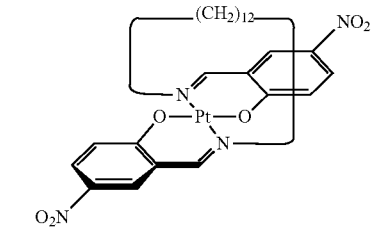 (u)
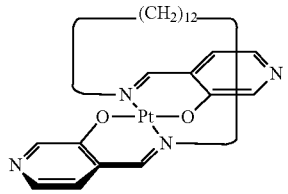 (v)
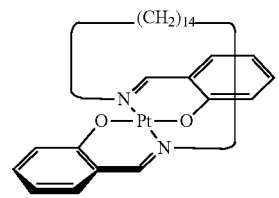 (w)
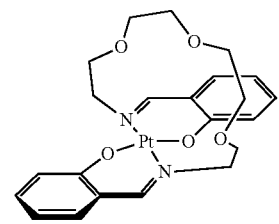 (x)
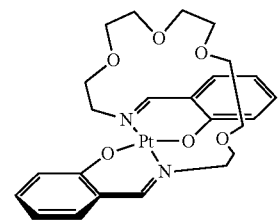 (y)
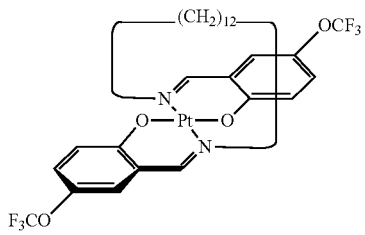 (z)
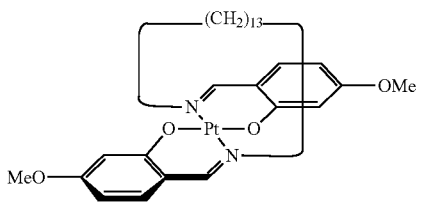 (aa)
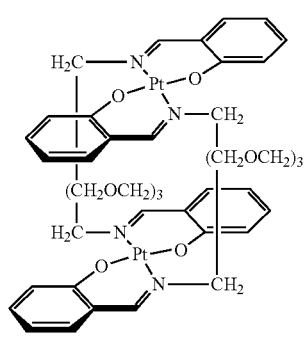 (ab)
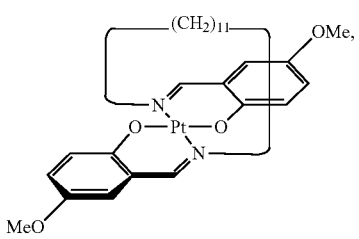 (ac)
[Chem. 4]
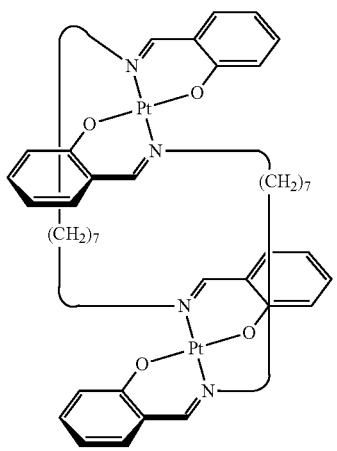 (af)

-continued

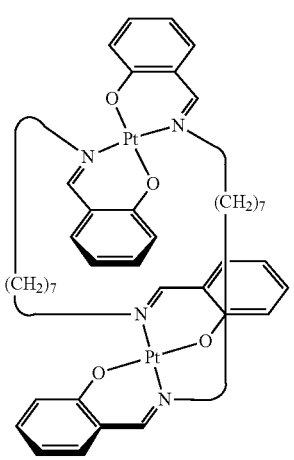
(ag)

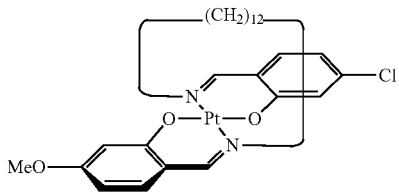
(aj)

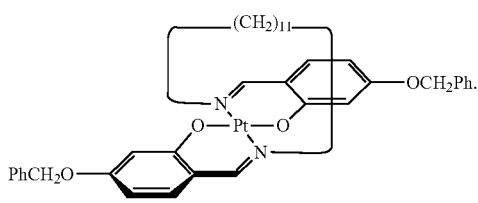
(ak)

In order to solve the above problem, a light-emitting material of the present invention includes: the light-emitting organic platinum complex represented by any one of the structural formulae above.

In order to solve the above problem, a functional device of the present invention includes: a pair of electrodes; and an organic layer sandwiched between the pair of electrodes, the organic layer including a light-emitting layer, the light-emitting layer including the light-emitting organic platinum complex represented by any one of the structural formulae above.

According to the above arrangement, the light-emitting organic platinum complex has ligands each having, introduced therein, a cross-linked structure formed by a cross-linking chain such as a methylene chain. This causes a nitrogen atom bonded to the cross-linking chain to be pulled toward the cross-linking chain. The light-emitting organic platinum complex thus has a three-dimensional structure (steric structure) in which the pair of ligands is bent with a platinum atom at the center. The ligands consequently cannot maintain a planar structure. This arrangement allows the light-emitting organic platinum complex to exhibit increased emission intensity that is sufficient for practical use even at room temperature (23° C.). The light-emitting organic platinum complex has increased emission intensity for the specific reasons that, for example, (i) the cross-linking chain formed as above changes (deforms) the coordination plane of the complex and (ii) the cross-linking chain controls accumulation between molecules of the light-emitting organic platinum complex. In addition, adjusting the length of the cross-linking chain can control the three-dimensional structure (steric structure) formed by the two ligands, and can thus control the color tone of light emission.

The light-emitting material having the above arrangement includes the light-emitting organic platinum complex represented by any one of the structural formulae above. The functional device having the above arrangement includes: a pair of electrodes; and an organic layer including a light-emitting layer, the organic layer being sandwiched between the pair of electrodes, the light-emitting layer including the light-emitting organic platinum complex represented by any one of the structural formulae above. The light-emitting material and the functional device are each (i) superior in luminous efficiency to conventional organometallic complexes and (ii) able to achieve emission intensity sufficient for practical use and produce all the three primary colors of light.

The above arrangement can thus provide (i) a light-emitting organic platinum complex that is superior in luminous efficiency to conventional organometallic complexes, that can achieve emission intensity sufficient for practical use, that can produce all the three primary colors of light, and that is useful as a material for a functional device such as an organic light-emitting element and (ii) a functional device including the light-emitting organic platinum complex.

Advantageous Effects of Invention

According to the light-emitting organic platinum complex of the present invention, the light-emitting material containing this complex, and the functional device containing this complex, it is advantageously possible to provide (i) a light-emitting organic platinum complex that is superior in luminous efficiency to conventional organometallic complexes, that can achieve emission intensity sufficient for practical use, that can produce all the three primary colors of light, and that is useful as a material for a functional device such as an organic light-emitting element, (ii) a light-emitting material containing the light-emitting organic platinum complex, and (iii) a functional device including the light-emitting organic platinum complex.

Platinum has richer deposits than does iridium, and is easy to obtain. The light-emitting organic platinum complex of the present invention is thus easier to industrialize than conventional organometallic complexes including iridium.

BRIEF DESCRIPTION OF DRAWINGS

FIG. 1 is an explanatory view illustrating a relation of a three-dimensional structure (steric structure), a color tone of light emission, and an emission intensity of a light-emitting organic platinum complex of the present invention.

DESCRIPTION OF EMBODIMENTS

The following explains one embodiment of the present invention. A light-emitting organic platinum complex of the present invention is represented by any of the following structural formulae (1), (2a) and (2b):

[Chem. 5]

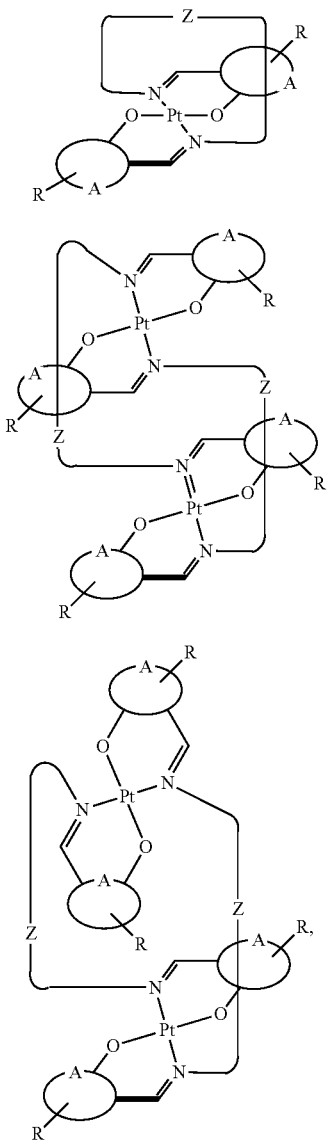

(In each of the above formulae, Z represents either —(CH$_2$)$_n$— or —CH$_2$(CH$_2$OCH$_2$)$_m$CH$_2$—, where n represents an integer of 7 to 14, and m represents either 3 or 4; A represents either an optionally condensed aromatic hydrocarbon ring or an optionally condensed heteroaromatic ring; R is a substituent group for A and represents hydrogen (unless n of Z in the structural formula (1) is 7 to 13), a halogen, an alkyl group having 1 to 6 carbon atoms, an alkenyl group having 1 to 6 carbon atoms, an alkynyl group having 1 to 6 carbon atoms, an alkoxy group having 1 to 6 carbon atoms, a halogenated alkoxy group represented by —OC$_p$H$_q$X$_r$, a hydroxyl group, a hydroxyethyl group, an alkyl amino group represented by —NR$_1$R$_2$, a nitro group, a sulfonyl group, a sulfinyl group, a carboxyl group, an acetoxy group, a ureido group, a phenyl group, an alkyl phenyl group having 7 to 13 carbon atoms, an alkyl phenyl oxy group having 7 to 13 carbon atoms, an alkynyl phenyl group having 8 to 13 carbon atoms, an alkenyl phenyl group having 8 to 13 carbon atoms, or a phenoxy group, where X represents a halogen, p represents an integer of 1 to 6, q represents 0 or a positive integer and satisfies "2p+1=q+r", r represents a positive integer and satisfies "2p+1=q+r", and R$_1$ and R$_2$ are each independently hydrogen or an alkyl group having 1 to 6 carbon atoms, a plurality of R being optionally present in A, the plurality of R present in A being optionally different from one another.)

In other words, the light-emitting organic platinum complex may be any of (a) a light-emitting organic platinum complex, as represented by the structural formula (1), containing one platinum atom, (b) a syn-type organoplatinum binuclear complex, as represented by the structural formula (2a), containing two platinum atoms, and (c) an anti-type organoplatinum binuclear complex, as represented by the structural formula (2b), containing two platinum atoms. Note that the light-emitting organic platinum complex may also be an organoplatinum trinuclear complex containing three platinum atoms.

Further, in a functional device of the present invention, the light-emitting organic platinum complex is represented by:
(a) the structural formula (1), where: Z is —(CH$_2$)$_n$—; n is an integer of 8 to 14; A is a benzene ring; and R is a halogen, a methyl group, an ethyl group, a methoxy group, an ethoxy group, a trifluoromethoxy group, a difluoromethoxy group, a hydroxyl group, a hydroxyethyl group, a dimethylamino group, a diethylamino group, a nitro group, an acetoxy group, a phenyl group, an alkyl phenyl oxy group having 7 to 13 carbon atoms, an alkynyl phenyl group having 8 to 13 carbon atoms, an alkenyl phenyl group having 8 to 13 carbon atoms, or (in a case of n=14) hydrogen;
(b) the structural formula (2a) or (2b), where: Z is —(CH$_2$)$_n$—; n is an integer of 7 to 14; A is a benzene ring; and R is hydrogen, a halogen, a methyl group, an ethyl group, a methoxy group, an ethoxy group, a trifluoromethoxy group, a difluoromethoxy group, a hydroxyl group, a hydroxyethyl group, a dimethylamino group, a diethylamino group, a nitro group, an acetoxy group, a phenyl group, an alkyl phenyl oxy group having 7 to 13 carbon atoms, an alkynyl phenyl group having 8 to 13 carbon atoms, or an alkenyl phenyl group having 8 to 13 carbon atoms;
(c) the structural formula (1), where: Z is —CH$_2$(CH$_2$OCH$_2$)$_m$ CH$_2$—; m represents 3 or 4; A is a benzene ring; and R is hydrogen, a halogen, a methyl group, an ethyl group, a methoxy group, an ethoxy group, a trifluoromethoxy group, a difluoromethoxy group, a hydroxyl group, a hydroxyethyl group, a dimethylamino group, a diethylamino group, a nitro group, an acetoxy group, a phenyl group, an alkyl phenyl oxy group having 7 to 13 carbon atoms, an alkynyl phenyl group having 8 to 13 carbon atoms, or an alkenyl phenyl group having 8 to 13 carbon atoms; or
(d) more preferably, the structural formula (2a) or (2b), where: Z is —CH$_2$(CH$_2$OCH$_2$)$_m$CH$_2$—; m represents 3 or 4; A is a benzene ring; and R is hydrogen, a halogen, a methyl group, an ethyl group, a methoxy group, an ethoxy group, a trifluoromethoxy group, a difluoromethoxy group, a hydroxyl group, a hydroxyethyl group, a dimethylamino group, a diethylamino group, a nitro group, an acetoxy group, a phenyl group, an alkyl phenyl oxy group having 7 to 13 carbon atoms, an alkynyl phenyl group having 8 to 13 carbon atoms, or an alkenyl phenyl group having 8 to 13 carbon atoms.

The light-emitting organic platinum complex may be synthesized by a synthesis method including the following two steps: (a) a synthesis step of synthesizing a ligand (hereinafter, referred to as a cross-linked ligand) into which a cross-linked structure is introduced by condensation of a ligand that is a base material and a material compound (hereinafter, referred to as a cross-linking compound) that introduces a cross-linked structure to two molecules of the ligand; and (b) an insertion step of inserting a platinum atom into the cross-linked ligand by using a platinum compound. Accordingly, the light-emitting organic platinum complex of the present invention can be synthesized more easily than, for example, a metalloporphyrin complex that is a conventional organometallic complex. The ligand above is a bidentate ligand. Accordingly, the cross-linked ligand functions as a quadridentate ligand with respect to a platinum atom.

More specifically, the following explains, as an example, a case where the light-emitting organic platinum complex is a light-emitting organic platinum complex represented by the above structural formula (1) and that is a trans-bis(salicylaldiminato) platinum complex. In this case, as shown in a reaction formula (A) below, the light-emitting organic platinum complex may be synthesized by a synthesis method including two steps: (i) the synthesis step of synthesizing N,N'-bis(salicylidene)-alkanediamine that is a cross-linked ligand obtained by condensation of 2 salicylaldehyde molecules that are ligands and 1 diaminoalkane molecule that is a cross-linking compound and (ii) the insertion step of inserting a platinum atom into N,N'-bis(salicylidene)-alkanediamine that becomes trans-bis(salicylaldimine) by using, for example, PtCl$_2$(CH$_3$CN)$_2$ that is a platinum compound.

[Chem. 6]

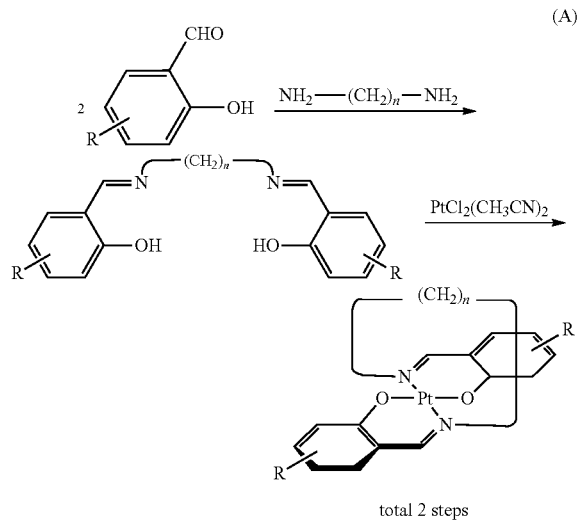

total 2 steps (In the above formula, R and n represent the same as described above.)

Alternatively, the synthesis step and the insertion step can be carried out in one pot substantially simultaneously. In the synthesis step in which two molecules of a ligand that is a didentate ligand are bound to each other (cross-linked) by one molecule of a cross-linking compound, a yield is 100% (or substantially 100%). Therefore, the above synthesis method is useful as an industrial production method.

The syn-type organoplatinum binuclear complex represented by the structural formula (2a) and the anti-type organoplatinum binuclear complex represented by the structural formula (2b) are obtained as by-products of the light-emitting organic platinum complex (mononuclear complex) represented by the structural formula (1). In other words, the organoplatinum binuclear complexes are produced as by-products in production of the light-emitting organic platinum complex (mononuclear complex). These organoplatinum binuclear complexes can be separated from the light-emitting organic platinum complex (mononuclear complex) by an operation of separation purification by means of, for example, column chromatography. Similarly, the organoplatinum trinuclear complex containing three platinum atoms can also be obtained as a by-product of the light-emitting organic platinum complex (mononuclear complex) represented by the structural formula (1). The organoplatinum trinuclear complex can be separated from the light-emitting organic platinum complex (mononuclear complex) by an operation of separation purification by means of, for example, column chromatography.

Note that in regard to the light-emitting organic platinum complex of the present invention, an optical isomer exists depending on a position of a cross-linked chain with respect to a coordination plane of the light-emitting organic platinum complex, that is, whether annulation of the cross-linked chain occurs on an upper side or a lower side of the coordination plane. In the above synthesis method, the light-emitting organic platinum complex is obtained as a racemic body.

The ligand constituting the light-emitting organic platinum complex may specifically be, for example: salicylaldehyde, 3-fluorosalicylaldehyde, 4-fluorosalicylaldehyde, 5-fluorosalicylaldehyde, 6-fluoro salicylaldehyde, 3-chlorosalicylaldehyde, 4-chlorosalicylaldehyde, 5-chlorosalicylaldehyde, 6-chlorosalicylaldehyde, 3-bromosalicylaldehyde, 4-bromosalicylaldehyde, 5-bromosalicylaldehyde, 6-bromosalicylaldehyde, 3-methylsalicylaldehyde, 4-methylsalicylaldehyde, 5-methylsalicylaldehyde, 6-methylsalicylaldehyde, 3-methoxysalicylaldehyde, 4-methoxysalicylaldehyde, 5-methoxysalicylaldehyde, 6-methoxysalicylaldehyde, 4,6-dimethoxysalicylaldehyde, 3-ethoxysalicylaldehyde, 4-ethoxysalicylaldehyde, 5-ethoxysalicylaldehyde, 6-ethoxysalicylaldehyde, 3-trifluoromethoxysalicylaldehyde, 4-trifluoromethoxysalicylaldehyde, 5-trifluoromethoxysalicylaldehyde, 6-trifluoromethoxysalicylaldehyde, 3-hydroxysalicylaldehyde, 4-hydroxysalicylaldehyde, 5-hydroxysalicylaldehyde, 6-hydroxysalicylaldehyde, 3-hydroxyethylsalicylaldehyde, 4-hydroxyethylsalicylaldehyde, 5-hydroxyethylsalicylaldehyde, 6-hydroxyethylsalicylaldehyde, 3-(diethylamino)salicylaldehyde, 4-(diethylamino)salicylaldehyde, 5-(diethylamino)salicylaldehyde, 6-(diethylamino)salicylaldehyde, 3-nitrosalicylaldehyde, 4-nitro salicylaldehyde, 5-nitrosalicylaldehyde, 6-nitro salicylaldehyde, 3-acetoxysalicylaldehyde, 4-acetoxysalicylaldehyde, 5-acetoxysalicylaldehyde, 6-acetoxysalicylaldehyde, 3-phenylsalicylaldehyde, 4-phenylsalicylaldehyde, 5-phenylsalicylaldehyde, 6-phenylsalicylaldehyde, 3-benzyloxysalicylaldehyde, 4-benzyloxysalicylaldehyde, 5-benzyloxysalicylaldehyde, 6-benzyloxysalicylaldehyde, 1-hydroxy-2-naphthoaldehyde, or 3-hydroxypyridine-4-carboxyaldehyde.

In other words, an aromatic hydrocarbon ring or a heteroaromatic ring that may be a condensed ring represented by "A" in the structural formulae (1), (2a), and (2b) is more preferably a benzene ring, a naphthalene ring (condensed ring), or a pyridine ring, and particularly preferably a benzene ring. Note that as is clear from the above structural formulae, there are various other ligands in addition to the above-described ligands provided as examples, in regard to the ligand constituting the light-emitting organic platinum complex of the present invention. In other words, the ligands provided as the examples above are merely specific examples.

The cross-linking compound may specifically be, for example: 1,7-diaminoheptane, 1,8-diaminooctane, 1,9-diaminononane, 1,10-diaminodecane, 1,11-diaminoundecane, 1,12-diaminododecane, 1,13-diaminotridecane, 1,14-diaminotetradecane, 1,11-diamino-3,6,9-trioxaundecane, or 1,14-diamino-3,6,9,12-tetraoxatetradecane. Note that the cross-linking compound constituting the light-emitting organic platinum complex of the present invention may be any compound as long as the compound enables the light-emitting organic platinum complex to construct a three-dimensional structure (steric structure). There are various other cross-linking compounds in addition to the above-described cross-linking compounds provided as examples. In other words, the cross-linking compounds provided as the examples above are merely specific examples.

The platinum compound may specifically be, for example, $PtCl_2(CH_3CN)_2$. However, the platinum compound is not particularly limited to this. As the platinum compound, a publicly known platinum compound that has been used for synthesizing a conventional organometallic complex may be suitably used.

In the above synthesis step, a publicly known solvent used for synthesis of a conventional Schiff base can be suitably used. The solvent may specifically be, for example, ethyl alcohol. However, the solvent is not limited to this. Further, in the insertion step, a publicly known solvent used for synthesizing a conventional organometallic complex may be suitably used. The solvent may specifically be, for example, a mixed solvent of toluene and dimethylsulfoxide. However, the solvent is not particularly limited to this. An amount of each of the solvent used with respect to ligands per unit quantity is not particularly limited. Further, in the insertion step, for accelerating a reaction, an inorganic compound such as potassium carbonate may be used at the same time.

For reaction conditions such as a reaction temperature, a reaction time, and the like in each of the synthesis step and the insertion step, it is possible to suitably employ publicly known reaction conditions employed for synthesizing a conventional organometallic complex. Further, after the synthesis step is completed, reaction solution is cooled and a cross-linked ligand may be taken out from the reaction solution. Further, after the insertion step is completed, reaction solution is condensed, and an operation for extraction and separation purification by means of, for example, column chromatography are carried out. Thereby, the light-emitting organic platinum complex can be taken out (isolated) in the form of, for example, a crystal. In other words, as a method for isolating the light-emitting organic platinum complex of the present invention, a publicly known isolation method used in isolation of a conventional organometallic complex can be suitably employed.

The light-emitting organic platinum complex of the present invention obtained by the above synthesis method is specifically represented more preferably by, for example, any of the structural formulae below. Therefore, as described above, the light-emitting organic platinum complex of the present invention encompasses an organoplatinum binuclear complex that contains two platinum atoms and that is represented by the structural formulae below. The light-emitting organic platinum complex represented by any of the structural formulae below is a novel substance that the inventors of the present invention first successfully synthesized. However, note that as is clear from the above synthesis method, the light-emitting organic platinum complex of the present invention is present in various ways in addition to the light-emitting organic platinum complex represented by any of the structural formulae below. In other words, the light-emitting organic platinum complex represented by any of the structural formulae below is merely a more preferable specific example of the light-emitting organic platinum complex. Further, the light-emitting organic platinum complex of the present invention also encompasses, for example, an organoplatinum trinuclear complex containing three platinum atoms.

[Chem. 7]

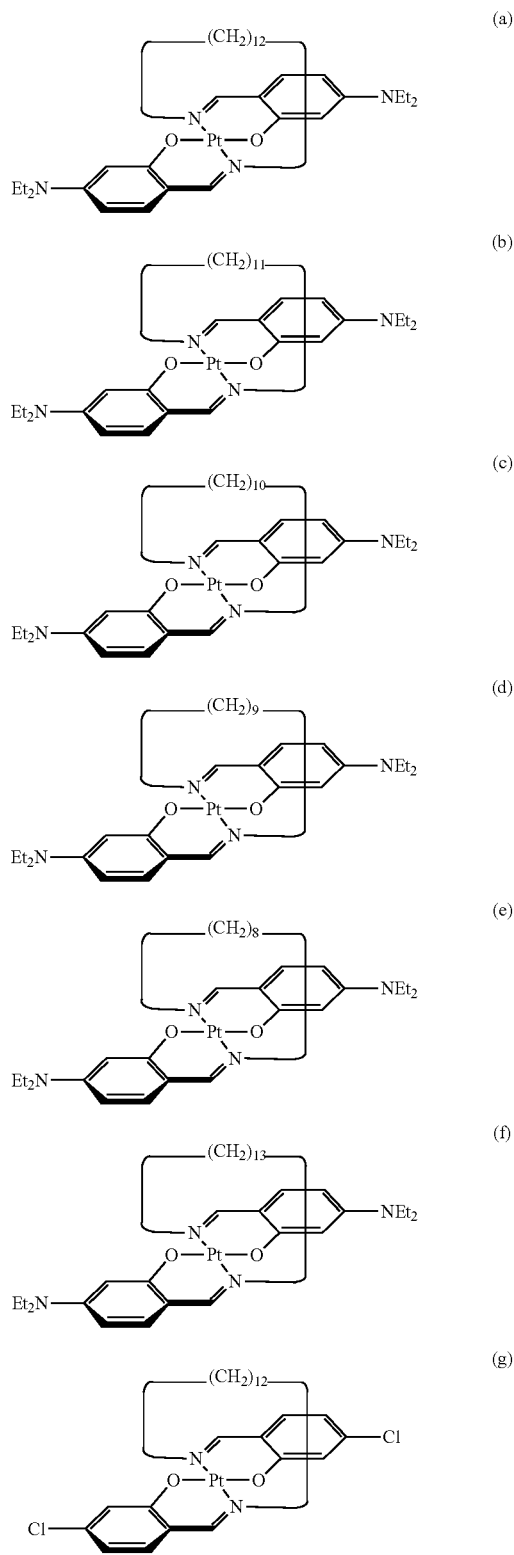

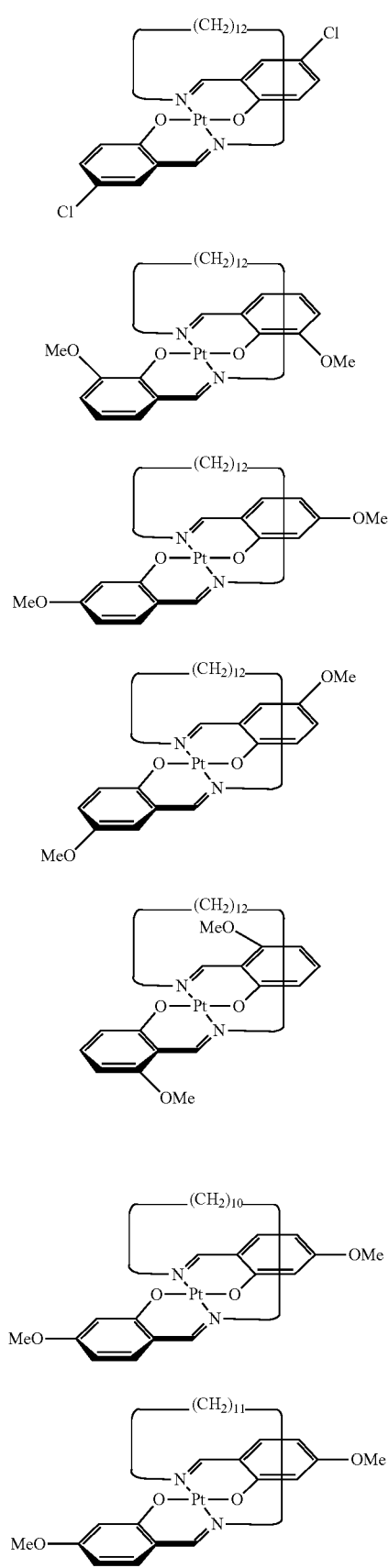
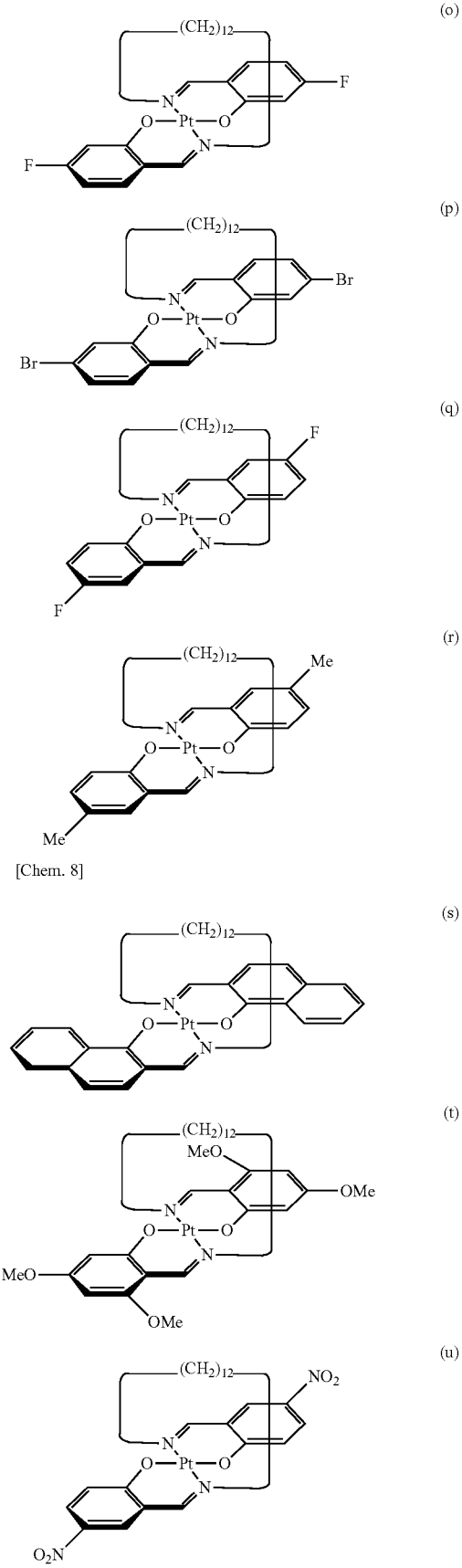

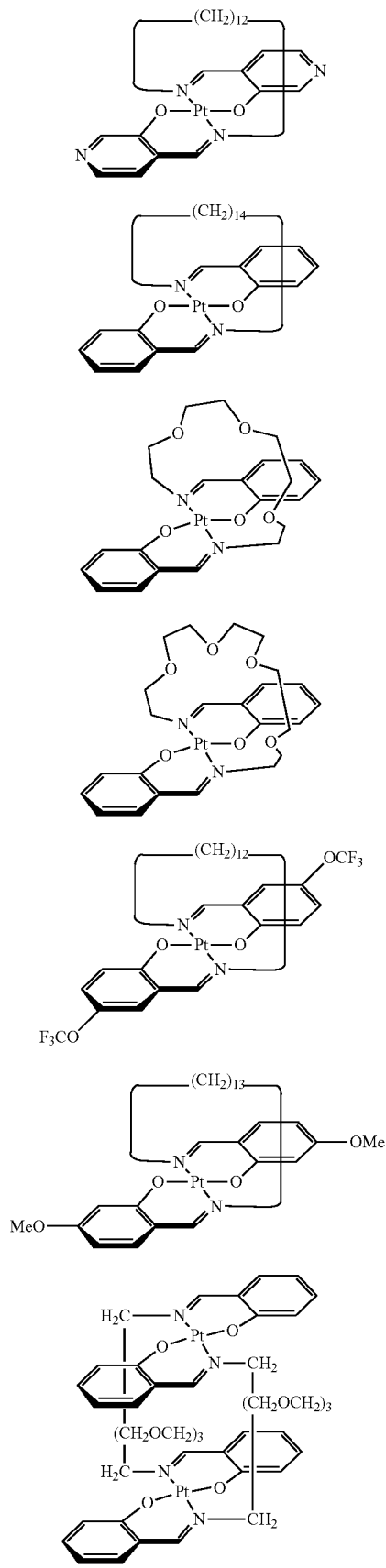
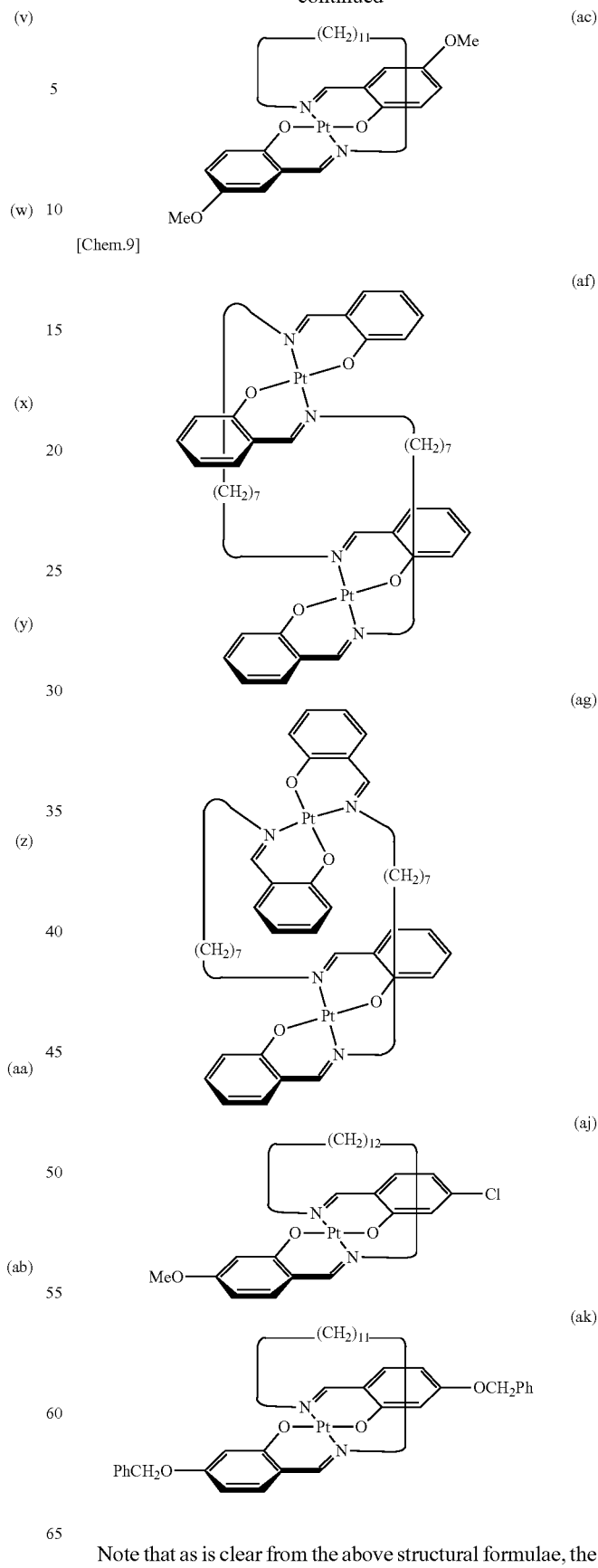
Note that as is clear from the above structural formulae, the light-emitting organic platinum complex of the present invention is represented more preferably by any of the above structural formulae (1), (2a), and (2b), where: Z is $-(CH_2)_n-$, where n is an integer of 8 to 14 in the case of the structural formula (1) or n is an integer of 7 to 14 in the case of the structural formulae (2a) and (2b); A is a benzene ring; and R is $-H$, $-F$, $-Cl$, $-Br$, $-CH_3$, $-OCH_3$, $-OCH_2C_6H_5$, $-N(C_2H_5)_2$, or $-NO_2$ (Note that in a case where n is an integer of 7 to 13 in the structural formula (1), R is not $-H$.). Alternatively, the light-emitting organic platinum complex of the present invention is represented more preferably by any of the above structural formulae (1), (2a), and (2b), where: Z is $-CH_2(CH_2OCH_2)_mCH_2-$, where m is 3 or 4; A is a benzene ring; and R is $-H$. Further, as is clear from the structural formula (aj), in the light-emitting organic platinum complex of the present invention, Rs present in A may be different from one another.

Next describes a relation between a three-dimensional structure (steric structure) and light-emission color tone, in the light-emitting organic platinum complex according to the present invention.

The light-emitting organic platinum complex exhibits phosphorescent light emission when switching over from a triplet transition state (excited triplet) to a ground state, due to a heavy-atom effect of the platinum atom. The light-emitting organic platinum complex according to the present invention has a cross-linked structure of a cross-linking chain (e.g. a methylene chain) introduced in a ligand of the light-emitting organic platinum complex, so hence a nitrogen atom bonded to the cross-linking chain is pulled toward the cross-linking chain. This causes the light-emitting organic platinum complex to take a three-dimensional structure (steric structure) in which a pair of two ligands is bent with the platinum atom as the center, thereby making it impossible for the ligand to maintain a planar structure. More specifically, the light-emitting organic platinum complex according to the present invention, by having two ligands have a cross-linked structure (i.e. a structure annulated near the platinum atom at the center of the complex) at a trans-position by the cross-linking chain, the light-emitting organic platinum complex has a three-dimensional structure (steric structure) in which the pair of two ligands is bent with the platinum atom at the center. Namely, the light-emitting organic platinum complex according to the present invention has two ligands be trans-coordinated, and a cross-linked structure is formed by nitrogen atoms of individual ligands, i.e. nitrogen atoms directly coordinated to the platinum atom. Hence, the rate of radiationless deactivation caused by molecular movement of the light-emitting organic platinum complex decreases (radiationless deactivation is held down).

Therefore, emission intensity of the light-emitting organic platinum complex increases, which causes the luminous efficiency of phosphorescence to increase; this allows for exhibiting emission intensity sufficient for practical use even at room temperature (23° C.). The light-emitting organic platinum complex has increased emission intensity for the specific reasons that, for example, (i) the cross-linking chain formed as above changes (deforms) the coordination plane of the complex and (ii) the cross-linking chain controls accumulation between molecules of the light-emitting organic platinum complex.

More specifically, by having the three-dimensional structure (steric structure), the individual light-emitting organic platinum complex molecules become of a non-accumulated form. This reduces the interaction between molecules in a solid state (crystal state or amorphous state). Consequently, the light-emitting organic platinum complex exhibits a high luminous efficiency (maximum solid light emitting quantum yield φ at 77K of 70%) in the solid state (crystal state or amorphous state).

The conventional organometallic complex whose ligands are of a planar structure have spaces upper and lower of the coordination plane of the complex molecule, and is of an accumulated form. As a result, it is difficult to dissolve and difficult to volatilize; thereby making it difficult to handle as a solid state. On the other hand, the molecules of the light-emitting organic platinum complex according to the present invention is of a non-accumulated form; for example, it is possible to apply a technique such as vapor deposition when producing the functional device, which is advantageous in an industrial manufacturing method.

Further, adjustment of a length (number of carbon atoms) of the cross-linking chain causes the light-emitting organic platinum complex according to the present invention to change (deform) in the coordination plane of the complex; this allows for controlling the three-dimensional structure (steric structure) of the two ligands. Accordingly, it is possible to control the emission wavelength of phosphorescence, i.e., the light-emission color tone and emission intensity.

The light-emission color tone and the emission intensity are described in more details. However, in the following description, for convenience, trans-bis(4-diethylamino salicylaldiminato) platinum complex (mononuclear complex) is used as an example of the light-emitting organic platinum complex, whose ligand is 4-diethylamino salicylaldimine, and whose cross-linking chain is a methylene chain.

More specifically, as illustrated in FIG. 1, trans-bis(4-diethylamino salicylaldiminato) platinum complex (R=4-N(C$_2$H$_5$)$_2$) changes in a bent angle of the two 4-diethylamino salicylaldimine ligands based on the length of the methylene chain (angle of one of the 4-diethylamino salicylaldimine ligands with respect to the other one of 4-diethylamino salicylaldimine ligands, and is 180° when the ligand is of a planar structure). Namely, when the length of the methylene chain is short, the nitrogen atom bonded to the methylene chain is strongly pulled toward the methylene chain. Hence, the two 4-diethylamino salicylaldimine ligands bend largely (length n of methylene chain=8, 9, 10). At this time, the light-emission color tone is a yellowish green color to a yellow color, and exhibits strong light emission at a low temperature (for example, 77K). On the other hand, when the length n of the methylene chain is 11 or 12, the degree that the two 4-diethylamino salicylaldimine ligands are bent is of a moderate level (the two 4-diethylamino salicylaldimine ligands are closer to a planar structure), and the light-emission color tone shifts over to a short wavelength, to a more yellowish green color. The degree of the bent state in the moderate level is the most stable structure of the light-emitting organic platinum complex. Hence, the light-emission intensity is the strongest at both room temperature and a low temperature (at room temperature, solid light emission quantum yield is high when the length n is 12, whereas at low temperature, the solid light emission quantum yield is high when the length n is 11 or 12). Moreover, when the length n of the methylene chain is even longer (n=13), the two 4-diethylamino salicylaldimine ligands become a substantially planar structure, and accumulation between molecules become partially possible. As a result, the light-emission color tone shifts to a longer wavelength, to a yellow color due to intermolecular interaction. Moreover, accumulation between molecules causes the emission intensity to be relatively small again. The planarity of the two 4-diethylamino salicylaldimine ligands is firmly maintained in the bent state or the planar state in accordance with the length of the methylene chain. Namely, trans-bis(4-diethylamino salicylaldiminato) platinum complex can have its three-dimensional structure (steric structure) be firmly fixed in any bent state by changing the length of the methylene chain. This hence allows for controlling the light-emission color tone and the emission intensity.

The three-dimensional structure (steric structure) of the light-emitting organic platinum complex can be clarified by single crystal X-ray structure analysis. For example, the bent angle of the two salicylaldimine ligands of trans-bis(salicylaldiminato) platinum complex in which R=H in FIG. 1, is 143° when n=7, and is 179° (substantially a planar structure) when n=13. Moreover, the angle may be found by performing molecule orbit calculation by density functional formalism.

The light-emitting organic platinum complex according to the present invention can be varied in the light-emission color tone between wavelengths (light emission maximum wavelength) of 514 nm to 663 nm, by changing the kind of ligand or its substituent group (substituent group represented by "R" in structural formulae (1), (2a), (2b)), or changing the kind and length of the cross-linking chain. Namely, with the light-emitting organic platinum complex according to the present invention, it is possible to obtain a wide range of light-emission color tone between colors from green to yellowish green, yellow, yellowish orange, orange, and up to red. Hence, by combining the light-emitting organic platinum complexes of these various light-emission color tones, it is possible to develop, for example, a white LED (light-emitting diode), which is a next-generation illumination, as a functional device.

Furthermore, the light-emitting organic platinum complex according to the present invention exhibits a strong light emission (phosphorescent light emission; $\tau=1.6$ μs) of a yellowish orange color having a wavelength of 550 nm, by for example, irradiating with, as excitation light, ultraviolet light having a wavelength of 365 nm or blue light having a wavelength of 420 nm. As a result of carrying out emitted-light color analysis, it was found that light emission of the yellowish-orange color has an extremely high color purity (CIE (0.49, 0.51), Pe 99%). Hence, a functional device including the light-emitting organic platinum complex according to the present invention can suitably be used in various apparatuses that require a single light.

The following description explains in detail of a light-emitting material and a functional device according to the present invention. The light-emitting material according to the present invention includes a light-emitting organic platinum complex represented by any one of the structural formulae (1), (2a) and (2b). Moreover, a functional device according to the present invention is a functional device that sandwiches, between a pair of electrodes, an organic layer including a light-emitting layer, the light-emitting layer including the light-emitting organic platinum complex represented by any one of the structural formulae (1), (2a), and (2b). Namely, the light-emitting material according to the present invention is, for example, suitably used as material for forming a light-emitting layer of the functional device according to the present invention.

More specifically, exemplifying a case in which the functional device is an organic EL element, the organic EL element is, for example, fabricated by stacking, on a substrate in the order mentioned, an anode, a hole injection layer and hole transport layer, a light-emitting layer including the light-emitting organic platinum complex, an electron injection layer and electron transport layer, and a cathode. Alternatively, the organic EL element is fabricated by, for example, stacking on a substrate in the order mentioned, a cathode, an electron injection layer and electron transport layer, a light-emitting layer including the light-emitting organic platinum complex, a hole injection layer and hole transport layer, and an anode. The hole injection layer, hole transport layer, light-emitting layer, electron injection layer, and electron transport layer are organic layers. Other organic layers may further be included other than the foregoing layers, such as a protective layer, a dielectric layer and the like provided in publicly known organic EL elements, if necessary. Namely, the organic EL element according to the present embodiment can suitably employ arrangements of publicly known organic EL elements for arrangements other than the light-emitting layer including the light-emitting organic platinum complex represented by any one of the foregoing structural formulae. However, in the present invention, just the light-emitting layer is an organic layer; even in a case in which other layers are of inorganic layers composed of an inorganic compound, such a case is also within the scope of the present invention. Namely, the functional device according to the present invention is sufficient as long as it includes at least the light-emitting layer as an organic layer.

The substrate may be made of any material as long as it allows transmission of light emitted from the light-emitting organic platinum complex without causing the light to scatter or attenuate. Specific examples of substrates suitably used as the substrate encompass a publicly known substrate made of inorganic material such as a glass substrate, or that made of organic material such as polyester, polystyrene, polycarbonate, or polyimide. The substrate may have a moisture transmission prevention layer or a gas barrier layer formed on its surface, if necessary.

The anode is sufficient as long as it is capable of supplying holes (positive holes) to the hole injection layer. Specific examples of publicly known material suitably used as the anode encompass various metals including alloys, metal oxides, or conductive compounds etc. Among these materials, the metal oxide is more preferably used, and a thin film made of iridium tin oxide (ITO) is particularly preferably used. Note that a publicly known forming method may be suitably employed as a method of forming the anode.

The cathode is sufficient as long as it is capable of supplying electrons to the electron injection layer. Specific examples of publicly known material suitably used as the cathode encompass various metals including alloys, metal oxides, or conductive compounds etc. Among these materials, (i) aluminum or (ii) an alloy of either alkali metal or alkali earth metal and aluminum is particularly preferable. Note that a publicly known forming method may be suitably employed as the method of forming the cathode.

In order to function as the organic EL element, it is desirable that at least one electrode (electrode formed on the substrate) of the anode and cathode is transparent.

The hole injection layer and the hole transport layer are sufficient as long as these are capable of receiving holes from the anode and transporting the holes to the light-emitting layer. As the hole injection layer and the hole transport layer, a publicly known material is suitably used. Note that a publicly known forming method may be suitably employed as the method of forming the hole injection layer and the hole transport layer.

The electron injection layer and the electron transport layer are sufficient as long as they are capable of receiving electrons from the cathode and transporting those electrons to the light-emitting layer. A publicly known material is suitably used as the electron injection layer and the electron transport layer. Note that a publicly known forming method may be suitably employed as the forming method of the electron injection layer and the electron transport layer.

The light-emitting layer is formed, for example, with light-emitting material according to the present invention, and is sufficient as long as it is capable of causing the light-emitting organic platinum complex to emit light, by bonding the hole transported from the anode via the hole injection layer and hole transport layer with electrons transported from the cathode via the electron injection layer and the electron transport layer, when a voltage is applied. The light-emitting layer may include host material, other than the light-emitting organic platinum complex. Namely, the light-emitting material may further include host material. The host material is material having at least one of the following functions: function of keeping the light-emitting organic platinum complex inside the light-emitting layer (i.e. light-emitting material) in a dispersed manner; function of receiving the holes and electrons; function of transporting the holes and electrons; function of bonding the holes and electrons; function of supplying (transmitting), to the light-emitting organic platinum complex, energy of exciton generated by the bonding; and the like. Publicly known material is suitably used as the host material. Among these materials, it is more preferable to use a mixture of a material having the hole transport function and a material having the electron transport function. Note that a publicly known forming method is suitably employed for the method of forming the light-emitting layer.

The voltage applied to the organic EL element of the foregoing arrangement is sufficient as, for example, approximately 6 V. However, this is not particularly limited. The organic EL element of the foregoing arrangement includes the light-emitting organic platinum complex represented by any one of the foregoing structural formulae, so hence it is possible to exhibit a wide range of light-emission color tones between colors from green to red. Namely, the functional device using the light-emitting organic platinum complex according to the present invention emits light with a wide range of light-emission color tones of colors between green and red, by applying a voltage.

Further, the functional device of the foregoing arrangement is configured in such a manner that an organic layer is sandwiched between a pair of electrodes, which organic layer includes a light-emitting layer including the light-emitting organic platinum complex represented by any one of the structural formulae (1), (2a), and (2b). This allows the light-emitting organic platinum complex to have luminous efficiency superior to conventional organometallic complexes and to be able to achieve emission intensity sufficient for practical use and produce all the three primary colors of light.

The above arrangement can thus provide (i) a light-emitting organic platinum complex that is superior in luminous efficiency to conventional organometallic complexes, that can achieve emission intensity sufficient for practical use, that can produce all the three primary colors of light, and that is useful as a material for a functional device such as an organic light-emitting element, (ii) a light-emitting material containing the light-emitting organic platinum complex, and (iii) a functional device containing the light-emitting organic platinum complex.

EXAMPLES

The following description deals with the present invention in more detail, with reference to Examples.

First provided below are synthesis examples of cross-linked ligands.

Synthesis Example 1

A combination of (i) 0.58 g of 4-(diethylamino)salicylaldehyde as a ligand and (ii) 0.3 g of 1,12-diaminododecane as a cross-linking compound was added to 5 ml of ethyl alcohol. The resulting mixture was refluxed while heated for 4 hours. The resulting reaction solution was cooled to room temperature, and then stirred in an ice-cold state. The resulting separated crystal was then filtered out, and dried under reduced pressure. This prepared 0.72 g of subtly yellow powder of N,N'-bis(4-diethylaminosalicylidene)-1,12-dodecanediamine as a cross-linked ligand.

$^1$H-NMR (270 MHz, CDCl$_3$) δ: 7.89 (2H, s) 6.94 (2H, d, J=8.6 Hz) 6.11 (2H, dd, J=8.9 Hz, 2.4 Hz) 6.05 (2H, d, J=2.4 Hz) 3.45 (4H, t, J=6.8 Hz) 3.36 (8H, q, J=6.8 Hz) 1.58-1.67 (4H, m) 1.25-1.40 (16H, m) 1.18 (12H, t, J=6.8 Hz)

Synthesis Example 2

With use of 0.58 g of 4-(diethylamino)salicylaldehyde and 0.28 g of 1,11-diaminoundecane, steps similar to those of Synthesis Example 1 were carried out to prepare 0.68 g of subtly yellow powder of N,N'-bis(4-diethylaminosalicylidene)-1,11-undecanediamine.

$^1$H-NMR (270 MHz, CDCl$_3$) δ: 13.9 (2H, br-s) 7.90 (2H, s) 6.95 (2H, d, J=8.9 Hz) 6.12 (2H, dd, J=8.9 Hz, 2.7 Hz) 6.06 (2H, d, J=2.7 Hz) 3.45 (4H, t, J=6.5 Hz) 3.36 (8H, q, J=6.8 Hz) 1.58-1.67 (4H, m) 1.26-1.40 (14H, m) 1.18 (12H, t, J=6.8 Hz)

Synthesis Example 3

With use of 0.58 g of 4-(diethylamino)salicylaldehyde and 0.26 g of 1,10-diaminodecane, steps similar to those of Synthesis Example 1 were carried out to prepare 0.71 g of subtly yellow powder of N,N'-bis(4-diethylaminosalicylidene)-1,10-decanediamine.

$^1$H-NMR (270 MHz, CDCl$_3$) δ: 13.9 (2H, br-s) 7.90 (2H, s) 6.95 (2H, d, J=8.9 Hz) 6.12 (2H, dd, J=8.9 Hz, 2.7 Hz) 6.06 (2H, d, J=2.7 Hz) 3.45 (4H, t, J=6.5 Hz) 3.36 (8H, q, J=6.8 Hz) 1.58-1.67 (4H, m) 1.26-1.40 (12H, m) 1.18 (12H, t, J=6.8 Hz)

Synthesis Example 4

With use of 0.58 g of 4-(diethylamino)salicylaldehyde and 0.24 g of 1,9-diaminononane, steps similar to those of Synthesis Example 1 were carried out to prepare 0.43 g of subtly yellow powder of N,N'-bis(4-diethylaminosalicylidene)-1,9-nonanediamine.

$^1$H-NMR (270 MHz, CDCl$_3$) δ: 7.89 (2H, s) 6.95 (2H, d, J=8.6 Hz) 6.11 (2H, dd, J=8.6 Hz, 2.7 Hz) 6.05 (2H, d, J=2.7 Hz) 3.44 (4H, t, J=7.0 Hz) 3.36 (8H, q, J=7.0 Hz) 1.49-2.18 (4H, m) 1.31-1.48 (10H, m) 1.18 (12H, t, J=7.0 Hz)

Synthesis Example 5

With use of 0.58 g of 4-(diethylamino)salicylaldehyde and 0.22 g of 1,8-diaminooctane, steps similar to those of Synthesis Example 1 were carried out to prepare 0.55 g of subtly yellow powder of N,N'-bis(4-diethylaminosalicylidene)-1,8-octanediamine.

$^1$H-NMR (270 MHz, CDCl$_3$) δ: 7.89 (2H, s) 6.95 (2H, d, J=8.9 Hz) 6.11 (2H, dd, J=8.9 Hz, 2.7 Hz) 6.05 (2H, d, J=2.7 Hz) 3.44 (4H, t, J=6.5 Hz) 3.36 (8H, q, J=7.3 Hz) 1.58-1.67 (4H, m) 1.32-1.41 (8H, m) 1.18 (12H, t, J=6.5 Hz)

Synthesis Example 6

With use of 0.58 g of 4-(diethylamino)salicylaldehyde and 0.32 g of 1,13-diaminotridecane, steps similar to those of Synthesis Example 1 were carried out to prepare 0.66 g of subtly yellow powder of N,N'-bis(4-diethylaminosalicylidene)-1,13-tridecanediamine.

$^1$H-NMR (270 MHz, CDCl$_3$) δ: 7.89 (2H, s) 6.95 (2H, d, J=8.9 Hz) 6.11 (2H, d, J=8.9 Hz, 2.7 Hz) 6.05 (2H, d, J=2.7 Hz) 3.45 (4H, t, J=6.8 Hz) 3.36 (8H, q, J=7.3 Hz) 1.25-1.67 (8H, m) 1.18 (12H, t, J=7.3 Hz) 1.18-1.25 (14H, m)

Synthesis Example 7

With use of 0.16 g of 4-chlorosalicylaldehyde and 0.10 g of 1,12-diaminododecane, steps similar to those of Synthesis Example 1 were carried out to prepare 0.23 g of subtly yellow powder of N,N'-bis(4-chlorosalicylidene)-1,12-dodecanediamine.

$^1$H-NMR (270 MHz, CDCl$_3$) δ: 14.1 (2H, br-s) 8.26 (2H, s) 7.13 (2H, d, J=8.1 Hz) 6.94 (2H, d, J=1.6 Hz) 6.80 (2H, dd, J=8.1 Hz, 1.6 Hz) 3.57 (4H, t, J=6.8 Hz) 1.60-1.71 (4H, m) 1.25-1.35 (16H, m)

Synthesis Example 8

With use of 0.47 g of 5-chlorosalicylaldehyde and 0.30 g of 1,12-diaminododecane, steps similar to those of Synthesis Example 1 were carried out to prepare 0.70 g of subtly yellow powder of N,N'-bis(5-chlorosalicylidene)-1,12-dodecanediamine.

$^1$H-NMR (270 MHz, CDCl$_3$) δ: 13.7 (2H, br-s) 8.25 (2H, s) 7.19-7.27 (4H, m) 6.99 (2H, d, J=8.4 Hz) 3.59 (4H, td, J=7.0 Hz, 1.1 Hz) 1.63-1.74 (4H, m) 1.25-1.48 (16H, m)

Synthesis Example 9

With use of 0.45 g of 3-methoxysalicylaldehyde and 0.30 g of 1,12-diaminododecane, steps similar to those of Synthesis Example 1 were carried out to prepare 0.60 g of subtly yellow powder of N,N'-bis(3-methoxysalicylidene)-1,12-dodecanediamine.

$^1$H-NMR (270 MHz, CDCl$_3$) δ: 14.2 (2H, br-s) 8.29 (2H, s) 6.83-6.92 (4H, m) 6.77 (2H, t, J=7.6 Hz) 3.90 (6H, s) 3.59 (4H, t, J=6.8 Hz) 1.62-1.74 (4H, m) 1.25-1.48 (16H, m)

Synthesis Example 10

With use of 0.45 g of 4-methoxysalicylaldehyde and 0.30 g of 1,12-diaminododecane, steps similar to those of Synthesis Example 1 were carried out to prepare 0.56 g of subtly yellow powder of N,N'-bis(4-methoxysalicylidene)-1,12-dodecanediamine.

$^1$H-NMR (270 MHz, CDCl$_3$) δ: 14.2 (2H, br-s) 8.09 (2H, s) 7.06 (2H, d, J=8.6 Hz) 6.37 (2H, d, J=2.7 Hz) 6.32 (2H, dd, J=8.6 Hz, 2.4 Hz) 3.80 (6H, s) 3.51 (4H, t, J=6.8 Hz) 1.61-1.80 (4H, m) 1.25-1.48 (16H, m)

Synthesis Example 11

With use of 0.45 g of 5-methoxysalicylaldehyde and 0.30 g of 1,12-diaminododecane, steps similar to those of Synthesis Example 1 were carried out to prepare 0.69 g of subtly yellow powder of N,N'-bis(5-methoxysalicylidene)-1,12-dodecanediamine.

$^1$H-NMR (270 MHz, CDCl$_3$) δ: 13.2 (2H, br-s) 8.29 (2H, s) 6.89-6.91 (4H, m) 6.76 (2H, t) 3.78 (6H, s) 3.58 (4H, td, J=7.0 Hz, 1.1 Hz) 1.58-1.74 (4H, m) 1.25-1.48 (16H, m)

Synthesis Example 12

With use of 0.45 g of 6-methoxysalicylaldehyde and 0.30 g of 1,12-diaminododecane, steps similar to those of Synthesis Example 1 were carried out to prepare 0.69 g of subtly yellow powder of N,N'-bis(6-methoxysalicylidene)-1,12-dodecanediamine.

$^1$H-NMR (270 MHz, CDCl$_3$) δ: 8.73 (2H, s) 7.20 (2H, t, J=8.1 Hz) 6.51 (2H, d, J=8.1 Hz) 6.22 (2H, d, J=8.1 Hz) 3.81 (6H, s) 3.55 (4H, t, J=7.0 Hz) 1.60-1.73 (4H, m) 1.20-1.45 (16H, m)

Synthesis Example 13

With use of 0.45 g of 4-methoxysalicylaldehyde and 0.26 g of 1,10-diaminodecane, steps similar to those of Synthesis Example 1 were carried out to prepare 0.55 g of subtly yellow powder of N,N'-bis(4-methoxysalicylidene)-1,10-decanediamine.

$^1$H-NMR (270 MHz, CDCl$_3$) δ: 14.2 (2H, br-s) 8.53 (2H, s) 7.06 (2H, d, J=8.6 Hz) 6.38 (2H, d, J=2.7 Hz) 6.33 (2H, dd, J=8.6 Hz, 2.7 Hz) 3.80 (6H, s) 3.51 (4H, t, J=6.9 Hz) 1.51-1.75 (4H, m) 1.20-1.48 (12H, m)

Synthesis Example 14

With use of 0.46 g of 4-methoxysalicylaldehyde and 0.28 g of 1,11-diaminoundecane, steps similar to those of Synthesis Example 1 were carried out to prepare 0.57 g of subtly yellow powder of N,N'-bis(4-methoxysalicylidene)-1,11-undecanediamine.

$^1$H-NMR (270 MHz, CDCl$_3$) δ: 14.2 (2H, br-s) 8.09 (2H, s) 7.06 (2H, d, J=8.6 Hz) 6.38 (2H, d, J=2.4 Hz) 6.33 (2H, dd, J=8.6 Hz, 2.4 Hz) 3.80 (6H, s) 3.51 (4H, t, J=6.6 Hz) 1.55-1.70 (4H, m) 1.25-1.48 (14H, m)

Synthesis Example 15

With use of 0.31 g of 4-fluorosalicylaldehyde and 0.22 g of 1,12-diaminododecane, steps similar to those of Synthesis Example 1 were carried out to prepare 0.41 g of subtly yellow powder of N,N'-bis(4-fluorosalicylidene)-1,12-dodecanediamine.

$^1$H-NMR (270 MHz, CDCl$_3$) δ: 14.3 (2H, br-s) 8.23 (2H, s) 7.17 (2H, dd, J=8.4 Hz, 6.5 Hz) 6.61 (2H, dd, J=10.8 Hz, 2.7 Hz) 6.52 (2H, ddd, J=8.4 Hz, 8.4 Hz, 2.7 Hz) 3.55 (4H, t, J=7.0 Hz) 1.56-1.74 (4H, m) 1.21-1.49 (16H, m)

Synthesis Example 16

With use of 0.44 g of 4-bromosalicylaldehyde and 0.22 g of 1,12-diaminododecane, steps similar to those of Synthesis Example 1 were carried out to prepare 0.56 g of subtly yellow powder of N,N'-bis(4-bromosalicylidene)-1,12-dodecanediamine.

$^1$H-NMR (270 MHz, CDCl$_3$) δ: 14.1 (2H, br-s) 8.25 (2H, s) 7.12 (2H, d, J=1.6 Hz) 7.06 (2H, d, J=7.8 Hz) 6.96 (2H, dd, J=7.8 Hz, 1.9 Hz) 3.56 (4H, t, J=6.8 Hz) 1.60-1.74 (4H, m) 1.20-1.39 (16H, m)

Synthesis Example 17

With use of 0.42 g of 5-fluorosalicylaldehyde and 0.30 g of 1,12-diaminododecane, steps similar to those of Synthesis Example 1 were carried out to prepare 0.64 g of subtly yellow powder of N,N'-bis(5-fluorosalicylidene)-1,12-dodecanediamine.

$^1$H-NMR (270 MHz, CDCl$_3$) δ: 13.4 (2H, br-s) 8.27 (2H, s) 6.86-7.05 (6H, m) 3.59 (4H, td, J=6.8 Hz, 1.1 Hz) 1.55-1.74 (4H, m) 1.21-1.45 (16H, m)

Synthesis Example 18

With use of 0.41 g of 5-methylsalicylaldehyde and 0.30 g of 1,12-diaminododecane, steps similar to those of Synthesis Example 1 were carried out to prepare 0.67 g of subtly yellow powder of N,N'-bis(5-methylsalicylidene)-1,12-dodecanediamine.

$^1$H-NMR (270 MHz, CDCl$_3$) δ: 13.4 (2H, br-s) 8.27 (2H, s) 7.09 (2H, dd, J=8.5 Hz, 1.9 Hz) 7.02 (2H, d, J=1.9 Hz) 6.85 (2H, d, J=8.5 Hz) 3.56 (4H, t, J=7.0 Hz) 2.28 (6H, s) 1.61-1.80 (4H, m) 1.25-1.48 (16H, m)

Synthesis Example 19

With use of 0.52 g of 1-hydroxy-2-naphthaldehyde and 0.30 g of 1,12-diaminododecane, steps similar to those of Synthesis Example 1 were carried out to prepare 0.49 g of subtly yellow powder of N,N'-bis(1-hydroxy-2-naphthylidene)-1,12-dodecanediamine.

$^1$H-NMR (270 MHz, CDCl$_3$) δ: 13.4 (2H, br-s) 8.46 (1H, s) 8.43 (1H, s) 7.74 (2H, d, J=10.5 Hz) 7.37-7.56 (6H, m) 6.92 (2H, d, J=8.9 Hz) 6.76 (2H, d, J=8.9 Hz) 3.51 (4H, m) 1.66-1.77 (4H, m) 1.21-1.40 (16H, m)

Synthesis Example 20

With use of 0.55 g of 4,6-dimethoxysalicylaldehyde and 0.30 g of 1,12-diaminododecane, steps similar to those of Synthesis Example 1 were carried out to prepare 0.43 g of subtly yellow powder of N,N'-bis(4,6-dimethoxysalicylidene)-1,12-dodecanediamine.

$^1$H-NMR (270 MHz, CDCl$_3$) δ: 14.2 (2H, br-s) 8.26 (2H, d, J=7.8 Hz) 5.85 (2H, d, J=2.2 Hz) 5.55 (2H, d, J=2.2 Hz) 3.77 (12H, s) 3.46 (4H, t, J=6.5 Hz) 1.60-1.72 (4H, m) 1.21-1.36 (16H, m)

Synthesis Example 21

With use of 0.50 g of 5-nitrosalicylaldehyde and 0.30 g of 1,12-diaminododecane, steps similar to those of Synthesis Example 1 were carried out to prepare 0.71 g of subtly yellow powder of N,N'-bis(5-nitrosalicylidene)-1,12-dodecanediamine.

$^1$H-NMR (270 MHz, CDCl$_3$) δ: 15.0 (2H, br-s) 8.31 (2H, s) 8.23 (2H, d, J=2.7 Hz) 8.18 (2H, dd, J=9.2 Hz, 2.7 Hz) 6.91 (2H, t, J=9.2 Hz) 3.66 (4H, t, J=6.8 Hz) 1.69-1.80 (4H, m) 1.25-1.48 (16H, m)

Synthesis Example 22

With use of 0.25 g of 3-hydroxypyridine-4-carboxaldehyde and 0.20 g of 1,12-diaminododecane, steps similar to those of Synthesis Example 1 were carried out to prepare 0.39 g of brown powder of N,N'-bis [(3-hydroxypyridine-4-yl)methylidene]-1,12-dodecanediamine.

$^1$H-NMR (270 MHz, CDCl$_3$) δ: 13.1 (2H, br-s) 8.43 (2H, s) 8.36 (2H, s) 8.19 (2H, d, J=4.9 Hz) 7.13 (2H, d, J=4.9 Hz) 3.65 (4H, t, J=7.0 Hz) 1.66-1.77 (4H, m) 1.20-1.48 (16H, m)

Synthesis Example 23

With use of 0.38 g of salicylaldehyde and 0.38 g of 1,14-diaminotetradecane, steps similar to those of Synthesis Example 1 were carried out to prepare 0.33 g of yellow solid of N,N'-bis(salicylidene)-1,14-tetradecanediamine.

$^1$H-NMR (500 MHz, CDCl$_3$) δ: 13.72 (2H, s) 8.33 (2H, s) 7.27-7.31 (2H, m) 7.24 (2H, dd, J=7.6 Hz, 1.6 Hz) 6.95 (2H, d, J=8.0 Hz) 6.86 (2H, td, J=7.5 Hz, 0.5 Hz) 3.58 (4H, t, J=6.9 Hz) 1.66-1.71 (4H, m) 1.20-1.40 (20H, m)

Synthesis Example 24

With use of 125 mg of salicylaldehyde and 105 mg of 1,11-diamino-3,6,9-trioxaundecane, steps similar to those of Synthesis Example 1 were carried out to prepare 210 mg of yellow oily substance of N,N'-bis(salicylidene)-3,6,9-trioxa-1,11-undecanediamine.

$^1$H-NMR (500 MHz, CDCl$_3$) δ: 13.43 (2H, s) 8.35 (2H, s) 7.28-7.31 (2H, m) 7.24 (2H, dd, J=7.7 Hz, 1.7 Hz) 6.95 (2H, d, J=8.2 Hz) 6.85-6.88 (2H, m) 3.72-3.75 (8H, m) 3.57-3.59 (8H, m)

Synthesis Example 25

With use of 0.36 g of salicylaldehyde and 0.54 g of 1,14-diamino-3,6,9,12-tetraoxatetradecane, steps similar to those of Synthesis Example 1 were carried out to prepare 0.21 g of yellow oily substance of N,N'-bis(salicylidene)-3,6,9,12-tetraoxa-1,14-tetradecanediamine.

$^1$H-NMR (500 MHz, CDCl$_3$) δ: 13.43 (6H, s) 8.36 (2H, s) 7.29 (2H, ddd, J=8.5 Hz, 7.0 Hz, 1.3 Hz) 7.25 (2H, dd, J=7.6 Hz, 1.7 Hz) 6.94 (2H, d, J=8.2 Hz) 6.86 (2H, td, J=7.5 Hz, 1.0 Hz) 3.56-3.76 (20H, m)

Synthesis Example 26

With use of 0.21 g of 5-trifluoromethoxysalicylaldehyde and 0.10 g of 1,12-diaminododecane, steps similar to those of Synthesis Example 1 were carried out to prepare 0.21 g of subtly yellow powder of N,N'-bis(5-trifluoromethoxysalicylidene)-1,12-dodecanediamine.

$^1$H-NMR (270 MHz, CDCl$_3$) δ: 13.4 (2H, br-s) 8.27 (2H, s) 7.11-7.18 (4H, m) 6.94 (2H, d, J=8.9 Hz) 3.59 (4H, t, J=6.8 Hz) 1.55-1.74 (4H, m) 1.21-1.45 (16H, m)

Synthesis Example 27

With use of 0.40 g of 4-methoxysalicylaldehyde and 0.10 g of 1,13-diaminotridecane, steps similar to those of Synthesis Example 1 were carried out to prepare 0.45 g of subtly yellow powder of N,N'-bis(4-methoxysalicylidene)-1,13-tridecanediamine.

$^1$H-NMR (270 MHz, CDCl$_3$) δ: 14.2 (2H, br-s) 8.09 (2H, s) 7.06 (2H, d, J=8.6 Hz) 6.37 (2H, d, J=2.4 Hz) 6.33 (2H, dd, J=8.6 Hz, 2.4 Hz) 3.75 (6H, s) 3.51 (4H, t, J=6.5 Hz) 1.55-1.73 (4H, m) 1.21-1.50 (18H, m)

Synthesis Example 28

A combination of 0.9 g of 4-methoxysalicylaldehyde and 1.2 g of 1,12-diaminododecane was added to 300 ml of ethyl alcohol. The resulting mixture was refluxed while heated for 30 minutes. The resulting reaction solution was concentrated under reduced pressure. The resulting yellow solid was filtered out. This yellow solid was dried under reduced pressure to 2.01 g of subtly yellow solid of N-(4-methoxysalicylidene)-1,12-dodecanediamine.

$^1$H-NMR (300 MHz, CDCl$_3$) δ: 8.10 (1H, s) 7.06 (1H, d, J=8.7 Hz) 6.38 (1H, d, J=2.7 Hz) 6.33 (1H, dd, J=8.7, 2.7 Hz) 3.80 (3H, s) 3.51 (2H, t, J=6.6 Hz) 2.68 (2H, t, J=6.6 Hz) 1.55-1.76 (2H, m) 1.20-1.50 (18H, m)

Next, 0.17 g of the above N-(4-methoxysalicylidene)-1,12-dodecanediamine and 0.8 g of 4-chlorosalicylaldehyde were dissolved in 7 ml of toluene. The resulting mixture was refluxed while heated overnight (for 12 hours). The resulting reaction solution was concentrated under reduced pressure. The resulting yellow solid was filtered out. This yellow solid was dried under reduced pressure to 0.23 g of subtly yellow powder of N-(4-methoxysalicylidene)-N'-(4-chlorosalicylidene)-1,12-dodecanediamine.

$^1$H-NMR (300 MHz, CDCl$_3$) δ: 14.1 (2H, br-s) 8.27 (1H, s) 8.10 (1H, s) 7.14 (1H, d, J=8.1 Hz) 7.14 (1H, d, J=8.7 Hz) 6.95 (1H, d, J=1.8 Hz) 6.80 (1H, dd, J=8.1, 1.8 Hz) 6.38 (1H, d, J=2.7 Hz) 6.33 (1H, dd, J=8.7, 2.7 Hz) 3.80 (3H, s) 3.57 (2H, t, J=6.9 Hz) 3.51 (2H, t, J=6.6 Hz) 1.45-1.75 (6H, m) 1.20-1.55 (14H, m)

Synthesis Example 29

With use of 0.4 g of 4-benzyloxysalicylaldehyde and 0.16 g of 1,11-diaminoundecane, steps similar to those of Synthesis Example 1 were carried out to prepare 0.48 g of subtly yellow powder of N,N'-bis(4-benzyloxysalicylidene)-1,11-diaminoundecane.

$^1$H-NMR (300 MHz, CDCl$_3$) δ: 14.2 (2H, br-s) 7.25-7.44 (10H, m) 7.07 (2H, d, J=8.7 Hz) 6.47 (2H, d, J=2.4 Hz) 6.41 (2H, dd, J=8.7, 2.4 Hz) 5.06 (4H, s) 3.51 (4H, t, J=6.6 Hz) 1.60-1.67 (4H, m) 1.25-1.45 (14H, m)

The description below deals with, as Examples, examples of synthesizing light-emitting organic platinum complexes including the above ligands.

Example 1

A combination of (i) 0.14 g of the N,N'-bis(4-diethylaminosalicylidene)-1,12-dodecanediamine synthesized in Synthesis Example 1, (ii) 0.23 g of potassium carbonate, and (iii) 0.09 g of PtCl$_2$(CH$_3$CN)$_2$ was added to a mixed solvent of 90 ml of toluene and 22.5 ml of dimethyl sulfoxide. The resulting mixture was refluxed while heated overnight (for 12 hours). The resulting reaction solution was then concentrated under reduced pressure. To the resulting residue, ethyl acetate and water were added to extract a target substance. The resulting organic layer was concentrated. The resulting crude product was refined by silica gel column chromatography (eluate; n-hexane:ethyl acetate=10:1). This prepared 53 mg of yellow powder of trans-bis(4-diethylaminosalicylaldiminato) platinum (II) complex represented by the structural formula (a).

$^1$H-NMR (500 MHz, CD$_3$CN) δ: 7.67 (2H, s) 7.05 (2H, d, J=8.9 Hz) 6.09 (2H, dd, J=8.9 Hz, 2.5 Hz) 5.99 (2H, d, J=2.5 Hz) 4.72-4.80 (2H, m) 3.33 (8H, q, J=7.1 Hz) 2.81-2.89 (2H, m) 2.04-2.10 (2H, m) 1.25-1.50 (18H, m) 1.13 (12H, t, J=7.1 Hz)

Example 2

With use of 0.14 g of the N,N'-bis(4-diethylaminosalicylidene)-1,11-undecanediamine synthesized in Synthesis Example 2, steps similar to those of Example 1 were carried out to prepare 40 mg of yellow powder of trans-bis(4-diethylaminosalicylaldiminato) platinum (II) complex represented by the structural formula (b).

$^1$H-NMR (500 MHz, CD$_3$CN) δ: 7.60 (2H, s) 7.01 (2H, d, J=8.9 Hz) 6.04 (2H, dd, J=8.9 Hz, 2.5 Hz) 5.93 (2H, d, J=2.5 Hz) 4.71-4.76 (2H, m) 3.30 (8H, q, J=7.1 Hz) 2.75-2.82 (2H, m) 2.10-2.19 (2H, m) 1.57-1.66 (2H, m) 1.33-1.57 (10H, m) 1.21-1.34 (2H, m) 1.09 (12H, t, J=7.1 Hz)

Example 3

With use of 0.14 g of the N,N'-bis(4-diethylaminosalicylidene)-1,10-decanediamine synthesized in Synthesis Example 3, steps similar to those of Example 1 were carried out to prepare 41 mg of yellow powder of trans-bis(4-diethylaminosalicylaldiminato) platinum (II) complex represented by the structural formula (c).

$^1$H-NMR (500 MHz, CD$_3$CN) δ: 7.61 (2H, s) 7.01 (2H, d, J=8.9 Hz) 6.04 (2H, dd, J=8.9 Hz, 2.5 Hz) 5.95 (2H, d, J=2.5 Hz) 4.66-4.72 (2H, m) 3.30 (8H, q, J=7.1 Hz) 2.82-2.89 (2H, m) 2.22-2.34 (2H, m) 1.68-1.75 (2H, m) 1.58-1.68 (2H, m) 1.47-1.57 (2H, m) 1.32-1.45 (4H, m) 1.25-1.32 (2H, m) 1.10 (12H, t, J=7.1 Hz)

Example 4

With use of 0.14 g of the N,N'-bis(4-diethylaminosalicylidene)-1,9-nonanediamine synthesized in Synthesis Example 4, steps similar to those of Example 1 were carried out to prepare 41 mg of yellow powder of trans-bis(4-diethylaminosalicylaldiminato) platinum (II) complex represented by the structural formula (d).

$^1$H-NMR (500 MHz, CD$_3$CN) δ: 7.61 (2H, s) 7.03 (2H, d, J=9.0 Hz) 6.07 (2H, dd, J=9.0 Hz, 2.5 Hz) 5.99 (2H, d, J=2.5 Hz) 4.64-4.72 (2H, m) 3.33 (8H, q, J=7.1 Hz) 3.03-3.09 (2H, m) 2.00-2.25 (2H, m) 1.75-1.90 (6H, m) 1.58-1.68 (2H, m) 1.38-1.47 (4H, m) 1.12 (12H, t, J=7.1 Hz)

MS (FAB): m/z 701.6 [M]$^+$

Example 5

With use of 0.14 g of the N,N'-bis(4-diethylaminosalicylidene)-1,8-octanediamine synthesized in Synthesis Example 5, steps similar to those of Example 1 were carried out to prepare 37 mg of yellow powder of trans-bis(4-diethylaminosalicylaldiminato) platinum (II) complex represented by the structural formula (e).

$^1$H-NMR (500 MHz, CD$_3$CN) δ: 7.57 (2H, s) 7.01 (2H, d, J=9.0 Hz) 6.06 (2H, dd, J=9.0 Hz, 2.5 Hz) 5.97 (2H, d, J=2.5 Hz) 4.59-4.63 (2H, m) 3.32 (8H, q, J=6.9 Hz) 3.02-3.08 (2H, m) 2.25-2.35 (2H, m) 1.97-2.05 (2H, m) 1.70-1.80 (2H, m) 1.25-1.40 (4H, m) 1.12 (12H, t, J=6.9 Hz)

MS (FAB): m/z 687.2 [M]$^+$

Example 6

With use of 0.42 g of the N,N'-bis(4-diethylaminosalicylidene)-1,13-tridecanediamine synthesized in Synthesis Example 6, steps similar to those of Example 1 were carried out to prepare 66 mg of yellow powder of trans-bis(4-diethylaminosalicylaldiminato) platinum (II) complex represented by the structural formula (f).

$^1$H-NMR (270 MHz, CDCl$_3$) δ: 7.54 (2H, s) 7.01 (2H, d, J=8.9 Hz) 6.04 (2H, s) 6.02 (2H, dd, J=8.9 Hz, 2.7 Hz) 4.79-4.88 (2H, m) 3.33 (8H, q, J=7.3 Hz) 2.68-2.80 (2H, m) 2.00-2.15 (2H, m) 1.25-1.65 (20H, m) 1.19 (12H, t, J=7.3 Hz)

MS (FAB): m/z 757.2 [M]$^+$

Example 7

With use of 0.11 g of the N,N'-bis(4-chlorosalicylidene)-1,12-dodecanediamine synthesized in Synthesis Example 7, steps similar to those of Example 1 were carried out to prepare 36 mg of yellow powder of trans-bis(4-chlorosalicylaldiminato) platinum (II) complex represented by the structural formula (g).

$^1$H-NMR (500 MHz, CD$_3$CN) δ: 7.99 (2H, s) 7.29 (2H, d, J=8.5 Hz) 6.90 (2H, d, J=1.9 Hz) 6.59 (2H, dd, J=8.5 Hz, 1.9

Hz) 4.71-4.77 (2H, m) 3.00 (2H, td, J=11.0 Hz, 3.4 Hz) 1.48-1.56 (2H, m) 1.30-1.45 (14H, m) 1.21-1.30 (2H, m) 1.06-1.12 (2H, m)

MS (FAB): m/z 670.2 [M]$^+$

Example 8

With use of 0.42 g of the N,N'-bis(5-chlorosalicylidene)-1,12-dodecanediamine synthesized in Synthesis Example 8, steps similar to those of Example 1 were carried out to prepare 150 mg of orange-colored powder of trans-bis(5-chlorosalicylaldiminato) platinum (II) complex represented by the structural formula (h).

$^1$H-NMR (270 MHz, CDCl$_3$) δ: 7.75 (2H, s) 7.19-7.26 (4H, m) 6.82 (2H, d, J=8.9 Hz) 4.84-4.92 (2H, m) 2.93 (2H, br-t, J=10.5 Hz) 2.10-2.25 (2H, m) 1.10-1.60 (18H, m)

MS (FAB): m/z 670.4 [M]$^+$

Example 9

With use of 0.42 g of the N,N'-bis(3-methoxysalicylidene)-1,12-dodecanediamine synthesized in Synthesis Example 9, steps similar to those of Example 1 were carried out to prepare 52 mg of orange-colored powder of trans-bis(3-methoxysalicylaldiminato) platinum (II) complex represented by the structural formula (i).

$^1$H-NMR (270 MHz, CDCl$_3$) δ: 7.82 (2H, s) 6.82-6.90 (4H, m) 6.50 (2H, t, J=8.1 Hz) 5.15-5.24 (2H, m) 3.81 (6H, m) 2.96 (2H, br-t, J=9.7 Hz) 2.21-2.25 (2H, m) 1.10-1.60 (18H, m)

MS (FAB): m/z 661.7 [M]$^+$

Example 10

With use of 0.14 g of the N,N'-bis(4-methoxysalicylidene)-1,12-dodecanediamine synthesized in Synthesis Example 10, steps similar to those of Example 1 were carried out to prepare 44 mg of orange-colored powder of trans-bis(4-methoxysalicylaldiminato) platinum (II) complex represented by the structural formula (j).

$^1$H-NMR (500 MHz, CD$_3$CN) δ: 7.87 (2H, s) 7.20 (2H, d, J=8.7 Hz) 6.36 (2H, d, J=2.3 Hz) 6.22 (2H, dd, J=8.7 Hz, 2.3 Hz) 4.76-4.82 (2H, m) 3.75 (6H, s) 2.95 (2H, td, J=11.2 Hz, 3.0 Hz) 1.20-1.62 (18H, m) 1.05-1.20 (2H, m)

MS (FAB): m/z 661.2 [M]$^+$

Example 11

With use of 0.14 g of the N,N'-bis(5-methoxysalicylidene)-1,12-dodecanediamine synthesized in Synthesis Example 11, steps similar to those of Example 1 were carried out to prepare 35 mg of red powder of trans-bis(5-methoxysalicylaldiminato) platinum (II) complex represented by the structural formula (k).

$^1$H-NMR (500 MHz, CD$_3$CN) δ: 7.95 (2H, s) 6.97 (2H, dd, J=9.2 Hz, 3.2 Hz) 6.81 (2H, d, J=3.2 Hz) 6.75 (2H, d, J=9.2 Hz) 4.78-4.84 (2H, m) 3.68 (6H, s) 2.97 (2H, td, J=10.8 Hz, 3.2 Hz) 1.45-1.54 (2H, m) 1.29-1.45 (14H, m) 1.21-1.29 (2H, m) 1.05-1.12 (2H, m)

MS (FAB): m/z 661.3 [M]$^+$

Example 12

With use of 0.42 g of the N,N'-bis(6-methoxysalicylidene)-1,12-dodecanediamine synthesized in Synthesis Example 12, steps similar to those of Example 1 were carried out to prepare 50 mg of yellow powder of trans-bis(6-methoxysalicylaldiminato) platinum (II) complex represented by the structural formula (l).

$^1$H-NMR (270 MHz, CDCl$_3$) δ: 8.34 (2H, s) 7.13 (2H, t, J=8.1 Hz) 6.50 (2H, d, J=8.1 Hz) 6.00 (2H, d, J=8.1 Hz) 4.81-4.92 (2H, m) 3.81 (6H, m) 2.98 (2H, br-t, J=10.3 Hz) 2.10-2.25 (2H, m) 1.10-1.60 (18H, m)

MS (FAB): m/z 661.7 [M]$^+$

Example 13

With use of 0.33 g of the N,N'-bis(4-methoxysalicylidene)-1,10-decanediamine synthesized in Synthesis Example 13, steps similar to those of Example 1 were carried out to prepare 190 mg of yellow powder of trans-bis(4-methoxysalicylaldiminato) platinum (II) complex represented by the structural formula (m).

$^1$H-NMR (270 MHz, CDCl$_3$) δ: 7.65 (2H, s) 7.08 (2H, d, J=8.9 Hz) 6.34 (2H, d, J=2.2 Hz) 6.20 (2H, dd, J=8.9 Hz, 2.2 Hz) 4.80-4.89 (2H, m) 3.78 (6H, s) 2.92 (2H, br-t, J=11.3 Hz) 2.04-2.48 (2H, m) 1.20-1.82 (14H, m)

MS (FAB): m/z 633.3 [M]$^+$

Example 14

With use of 0.40 g of the N,N'-bis(4-methoxysalicylidene)-1,11-undecanediamine synthesized in Synthesis Example 14, steps similar to those of Example 1 were carried out to prepare 80 mg of yellow powder of trans-bis(4-methoxysalicylaldiminato) platinum (II) complex represented by the structural formula (n).

$^1$H-NMR (270 MHz, CDCl$_3$) δ: 7.65 (2H, s) 7.08 (2H, d, J=8.9 Hz) 6.34 (2H, d, J=2.2 Hz) 6.20 (2H, dd, J=8.9 Hz, 2.2 Hz) 4.80-4.89 (2H, m) 3.78 (6H, s) 2.92 (2H, br-t, J=11.3 Hz) 2.04-2.48 (2H, m) 1.20-1.82 (14H, m)

MS (FAB): m/z 647.4 [M]$^+$

Example 15

With use of 0.35 g of the N,N'-bis(4-fluorosalicylidene)-1,12-dodecanediamine synthesized in Synthesis Example 15, steps similar to those of Example 1 were carried out to prepare 170 mg of yellow powder of trans-bis(4-fluoro salicylaldiminato) platinum (II) complex represented by the structural formula (o).

$^1$H-NMR (270 MHz, CDCl$_3$) δ: 7.75 (2H, s) 7.20 (2H, td, J=8.6 Hz, 1.6 Hz) 6.55 (2H, dd, J=11.3 Hz, 2.7 Hz) 6.35 (2H, td, J=8.6 Hz, 2.7 Hz) 4.80-4.91 (2H, m) 2.92 (2H, br-t, J=10.5 Hz) 2.11-2.19 (2H, m) 1.10-1.60 (18H, m)

MS (FAB): m/z 637.5 [M]$^+$

Example 16

With use of 0.42 g of the N,N'-bis(4-bromosalicylidene)-1,12-dodecanediamine synthesized in Synthesis Example 16, steps similar to those of Example 1 were carried out to prepare 150 mg of yellow powder of trans-bis(4-bromosalicylaldiminato) platinum (II) complex represented by the structural formula (p).

$^1$H-NMR (270 MHz, CDCl$_3$) δ: 7.77 (2H, s) 7.09 (2H, d, J=1.9 Hz) 7.07 (2H, d, J=8.6 Hz) 6.71 (2H, dd, J=8.6 Hz, 1.9 Hz) 4.82-4.88 (2H, m) 2.92 (2H, br-t, J=9.7 Hz) 2.10-2.22 (2H, m) 1.10-1.60 (18H, m)

MS (FAB): m/z 760.4 [M]$^+$

Example 17

With use of 0.44 g of the N,N'-bis(5-fluorosalicylidene)-1, 12-dodecanediamine synthesized in Synthesis Example 17, steps similar to those of Example 1 were carried out to prepare 102 mg of reddish orange powder of trans-bis(5-fluoro salicylaldiminato) platinum (II) complex represented by the structural formula (q).

$^1$H-NMR (270 MHz, CDCl$_3$) δ: 7.74 (2H, s) 7.08 (2H, td, J=8.6 Hz, 3.0 Hz) 6.91 (2H, dd, J=8.6 Hz, 3.0 Hz) 6.81 (2H, dd, J=8.6 Hz, 4.9 Hz) 4.87-4.94 (2H, m) 2.93 (2H, br-t, J=10.0 Hz) 2.11-2.20 (2H, m) 1.10-1.70 (18H, m)

Example 18

With use of 0.42 g of the N,N'-bis(5-methylsalicylidene)-1,12-dodecanediamine synthesized in Synthesis Example 18, steps similar to those of Example 1 were carried out to prepare 130 mg of reddish orange powder of trans-bis(5-methyl salicylaldiminato) platinum (II) complex represented by the structural formula (r).

$^1$H-NMR (270 MHz, CDCl$_3$) δ: 7.78 (2H, s) 7.13 (2H, dd, J=8.6 Hz, 2.7 Hz) 7.01 (2H, d, J=2.7 Hz) 6.81 (2H, dd, J=8.6 Hz) 4.91-4.97 (2H, m) 2.91 (2H, br-t, J=11.9 Hz) 2.24 (6H, s) 2.12-2.25 (2H, m) 1.10-1.60 (18H, m)

Example 19

With use of 0.10 g of the N,N'-bis(1-hydroxy-2-naphthylidene)-1,12-dodecanediamine synthesized in Synthesis Example 19, steps similar to those of Example 1 were carried out to prepare 33 mg of orange-colored powder of trans-bis (1-hydroxy-2-naphthylaldiminato) platinum (II) complex represented by the structural formula (s).

$^1$H-NMR (270 MHz, CDCl$_3$) δ: 8.34 (2H, d, J=8.6 Hz) 7.92 (2H, s) 7.62-7.68 (2H, m) 7.57 (2H, td, J=6.6 Hz, 1.0 Hz) 7.42 (2H, td, J=8.3 Hz, 1.3 Hz) 7.23 (2H, d, J=8.6 Hz) 7.00 (2H, d, J=8.6 Hz) 5.12-5.24 (2H, m) 3.12 (2H, br-t, J=10.2 Hz) 2.34-2.50 (2H, m) 1.25-1.75 (16H, m) 0.98-1.20 (2H, m)

MS (FAB): m/z 701.8 [M]$^+$

Example 20

With use of 0.14 g of the N,N'-bis(4,6-dimethoxysalicylidene)-1,12-dodecanediamine synthesized in Synthesis Example 20, steps similar to those of Example 1 were carried out to prepare 35 mg of yellow powder of trans-bis(4,6-dimethoxysalicylaldiminato) platinum (II) complex represented by the structural formula (t).

$^1$H-NMR (270 MHz, CDCl$_3$) δ: 8.17 (2H, s) 5.98 (2H, d, J=1.9 Hz) 5.66 (2H, d, J=2.2 Hz) 4.80 (2H, br-d, J=11.1 Hz) 3.78 (12H, s) 3.77 (6H, s) 2.93 (2H, br-t, J=12.1 Hz) 2.10-2.25 (2H, m) 1.05-1.60 (18H, m)

Example 21

With use of 0.20 g of the N,N'-bis(5-nitrosalicylidene)-1,12-dodecanediamine synthesized in Synthesis Example 21, steps similar to those of Example 1 were carried out to prepare 14 mg of yellow powder of trans-bis(5-nitrosalicylaldiminato) platinum (II) complex represented by the structural formula (u).

$^1$H-NMR (270 MHz, DMSO-d$_6$) δ: 8.59 (2H, d, J=3.0 Hz) 8.58 (2H, s) 8.20 (2H, dd, J=9.2 Hz, 3.0 Hz) 6.99 (2H, d, J=9.2 Hz) 4.60-4.75 (2H, m) 3.18 (2H, br-t, J=8.1 Hz) 1.85-2.15 (2H, m) 1.50-1.68 (2H, m) 1.10-1.48 (16H, m)

MS (FAB): m/z 691.1 [M]$^+$

Example 22

With use of 0.20 g of the N,N'-bis [(3-hydroxypyridine-4-yl)methylidene]-1,12-dodecanediamine synthesized in Synthesis Example 22, steps similar to those of Example 1 were carried out to prepare 12 mg of red powder of trans-bis(4-aza aldiminato) platinum (II) complex represented by the structural formula (v).

$^1$H-NMR (270 MHz, CDCl$_3$) δ: 8.37 (2H, s) 7.89 (2H, s) 7.81 (2H, d, J=5.3 Hz) 7.09 (2H, d, J=5.3 Hz) 4.94-5.01 (2H, m) 3.01 (2H, br-t, J=10.6 Hz) 2.05-2.30 (2H, m) 1.10-1.73 (18H, m)

MS (FAB): m/z 603.3 [M]$^+$

Example 23

With use of 0.44 g of the N,N'-bis(salicylidene)-1,14-tetradecanediamine synthesized in Synthesis Example 23, steps similar to those of Example 1 were carried out to prepare 88 mg of yellow powder of trans-bis(salicylaldiminato) platinum (II) complex represented by the structural formula (w).

$^1$H-NMR (500 MHz, CDCl$_3$) δ: 7.86 (2H, s) 7.31 (2H, td, J=7.6 Hz, 1.7 Hz) 7.24 (2H, dd, J=7.9 Hz, 1.7 Hz) 6.89 (2H, d, J=8.5 Hz) 6.57 (2H, td, J=7.4 Hz, 0.93 Hz) 4.88-4.93 (2H, m) 2.88-2.96 (2H, m) 1.93-2.04 (2H, m) 1.71-1.82 (2H, m) 1.04-1.50 (20H, m)

Example 24

With use of 0.47 g of the N,N'-bis(salicylidene)-3,6,9-trioxa-1,11-undecanediamine synthesized in Synthesis Example 24, steps similar to those of Example 1 were carried out to prepare 178 mg of yellow powder of trans-bis(salicylaldiminato) platinum (II) complex represented by the structural formula (x).

$^1$H-NMR (500 MHz, CDCl$_3$) δ: 7.89 (2H, s) 7.31 (2H, ddd, J=8.0 Hz, 6.5 Hz, 1.5 Hz) 7.24-7.80 (2H, m) 6.86 (2H, d, J=8.5 Hz) 6.57 (2H, ddd, J=8.0 Hz, 6.5 Hz, 0.5 Hz) 5.04-5.10 (2H, m) 4.27 (2H, ddd, J=11.0 Hz, 8.5 Hz, 3.0 Hz) 3.88-3.94 (2H, m) 3.78-3.84 (2H, m) 3.65-3.74 (6H, m) 3.09-3.14 (2H, m)

Example 25

With use of 0.23 g of the N,N'-bis(salicylidene)-3,6,9,12-tetraoxa-1,14-tetradecanediamine synthesized in Synthesis Example 25, steps similar to those of Example 1 were carried out to prepare 46 mg of yellow powder of trans-bis(salicylaldiminato) platinum (II) complex represented by the structural formula (y).

$^1$H-NMR (500 MHz, CDCl$_3$) δ: 7.92 (2H, s) 7.33 (2H, td, J=7.8 Hz, 1.6 Hz) 7.26-7.29 (2H, m) 6.87 (2H, d, J=8.5 Hz) 6.59 (2H, td, J=7.4 Hz, 0.9 Hz) 4.88 (2H, d, J=8.5 Hz) 3.99-4.07 (4H, m) 3.74-3.78 (2H, m) 3.53-3.67 (8H, m) 3.07-3.16 (4H, m)

Example 26

With use of 0.14 g of the N,N'-bis(5-trifluoromethoxysalicylidene)-1,12-dodecanediamine synthesized in Synthesis Example 26, steps similar to those of Example 1 were carried out to prepare 10 mg of orange-colored powder of trans-bis (5-trifluoromethoxysalicylaldiminato) platinum (II) complex represented by the structural formula (z).

$^1$H-NMR (270 MHz, CDCl$_3$) δ: 13.4 (2H, br-s) 8.27 (2H, s) 6.86-7.05 (6H, m) 3.59 (4H, td, J=6.8 Hz, 1.1 Hz) 1.55-1.74 (4H, m) 1.21-1.45 (16H, m)

Example 27

With use of 0.36 g of the N,N'-bis(4-methoxysalicylidene)-1,13-tridecanediamine synthesized in Synthesis Example 27, steps similar to those of Example 1 were carried out to prepare 60 mg of yellow powder of trans-bis(4-methoxysalicylaldiminato) platinum (II) complex represented by the structural formula (aa).

$^1$H-NMR (270 MHz, CDCl$_3$) δ: 7.68 (2H, s) 7.11 (2H, d, J=8.6 Hz) 6.34 (2H, d, J=2.4 Hz) 6.21 (2H, dd, J=8.6 Hz, 2.4 Hz) 4.82-4.91 (2H, m) 3.79 (6H, s) 2.82 (2H, td, J=10.8 Hz, 4.1 Hz) 1.98-2.16 (2H, m) 1.60-1.70 (2H, m) 1.15-1.49 (18H, m)

Example 28

A by-product resulting from the synthesis of the trans-bis (salicylaldiminato) platinum (II) complex in Example 24 was refined by silica gel column chromatography (eluate; n-hexane:ethyl acetate=10:1) for isolation. This prepared 14 mg of yellow powder of trans-bis(salicylaldiminato) platinum (II) binuclear complex represented by the structural formula (ab).

$^1$H-NMR (500 MHz, CDCl$_3$) δ: 7.93 (s, 4H, N=CH) 7.29-7.22 (m, 4H, H$^4$, H$^6$), 6.84 (d, J=8.6 Hz, 4H, H$^3$) 6.51 (t, J=7.3 Hz, 4H, H$^5$) 4.09-3.37 (m, 32H)

MS (FAB): m/z 1168.3 [M+H]$^+$

Example 29

With use of 194 mg of N,N'-bis(salicylidene)-1,7-heptanediamine, steps similar to those of Example 1 were carried out to synthesize trans-bis(salicylaldiminato) platinum (II) complex. A by-product resulting from this synthesis was refined by silica gel column chromatography (eluate; n-hexane:ethyl acetate=10:1) for isolation. This prepared 9 mg of orange-colored powder of syn-type trans-bis(salicylaldiminato) platinum (II) binuclear complex represented by the structural formula (af).

$^1$H-NMR (270 MHz, CDCl$_3$) δ: 7.77 (4H, s) 7.14 (8H, d, J=7.0 Hz) 6.80 (4H, d, J=8.4 Hz) 6.47 (4H, ddd, J=7.0 Hz, 4.3 Hz, 1.1 Hz) 4.64 (4H, ddd, J=10.8 Hz, 5.4 Hz, 5.4 Hz) 3.00 (4H, ddd, J=11.0 Hz, 11.0 Hz, 8.1 Hz) 1.56-1.90 (8H, m) 1.36-1.48 (12H, m)

Example 30

Steps similar to those of Example 29 were carried out to prepare 29 mg of red powder of anti-type trans-bis(salicylaldiminato) platinum (II) binuclear complex represented by the structural formula (ag).

$^1$H-NMR (270 MHz, CDCl$_3$) δ: 7.61 (4H, s) 7.32 (4H, ddd, J=8.4 Hz, 6.8 Hz, 1.9 Hz) 7.13 (4H, dd, J=7.6 Hz, 1.6 Hz) 6.86 (4H, d, J=7.6 Hz) 6.57 (4H, ddd, J=8.1 Hz, 7.0 Hz, 1.1 Hz) 4.65 (4H, ddd, J=11.0 Hz, 11.0 Hz, 7.0 Hz) 2.80-2.89 (4H, m) 1.81-1.93 (8H, m) 1.42-1.74 (12H, m)

Example 31

A combination of (i) 0.18 g of N-(4-methoxysalicylidene)-N'-(4-chlorosalicylidene)-1,12-dodecanediamine synthesized in Synthesis Example 28, (ii) 0.52 g of potassium carbonate, and (iii) 0.13 g of PtCl$_2$(CH$_3$CN)$_2$ was added to a mixed solvent of 180 ml of toluene and 45 ml of dimethyl sulfoxide. The resulting mixture was refluxed while heated overnight (for 12 hours). The resulting reaction solution was then concentrated under reduced pressure. To the resulting residue, ethyl acetate and water were added to extract a target substance. The resulting organic layer was concentrated. The resulting crude product was refined by silica gel column chromatography (eluate; n-hexane:ethyl acetate=10:1). This prepared 60 mg of yellow powder of trans-(4-methoxy-4'-chlorosalicylaldiminato) platinum (II) complex represented by the structural formula (aj).

$^1$H-NMR (300 MHz, CDCl$_3$) δ: 7.80 (1H, s) 7.67 (1H, s) 7.15 (1H, d, J=8.4 Hz) 7.12 (1H, d, J=8.7 Hz) 6.90 (1H, d, J=1.8 Hz) 6.55 (1H, dd, J=8.4, 1.8 Hz) 6.35 (1H, d, J=2.4 Hz) 6.23 (1H, dd, J=8.7, 2.4 Hz) 6.33 (1H, dd, J=8.7, 2.7 Hz) 4.91-4.99 (1H, m) 4.76-4.86 (1H, m) 3.80 (3H, s) 2.84-2.90 (2H, m) 2.05-2.25 (2H, m) 1.25-1.60 (16H, m) 1.10-1.24 (2H, m)

Example 32

With use of 0.4 g of the N,N'-bis(4-benzyloxysalicylidene)-1,11-diaminoundecane synthesized in Synthesis Example 29, steps similar to those of Example 1 were carried out to prepare 120 mg of yellow powder of trans-bis(4-benzyloxysalicylaldiminato) platinum (II) complex represented by the structural formula (ak).

$^1$H-NMR (300 MHz, CDCl$_3$) δ: 7.65 (2H, s) 7.25-7.45 (10H, m) 7.11 (2H, d, J=8.7 Hz) 6.46 (2H, d, J=2.4 Hz) 6.28 (2H, dd, J=8.7, 2.4 Hz) 5.03 (4H, s) 4.88-4.94 (2H, m) 1.58-1.67 (4H, m) 2.86 (2H, t, J=9.6 Hz) 2.23-2.30 (2H, m) 1.19-1.64 (16H, m)

[Measurement of Solid Light Emission Quantum Yield]

Measurements were made of respective solid light-emission quantum yields φ (%) at 296K and 77K of the light-emitting organic platinum complexes prepared in Examples 1 through 32. Specifically, measurements were made, by an absolute method, of a light-emission quantum yield of each light-emitting organic platinum complex in a crystalline state (powder). The measurements were made by the method below.

(Measurement Method)

The measurements used fluoro-photometer FP-6500N, phosphorescence-measuring low-temperature integrating sphere system INK-533, and liquid sample cell LPH-120 (all available from JASCO Corporation). To avoid influence of oxygen, all samples (light-emitting organic platinum complexes) were (i) sealed in a quartz cell while the samples were in the crystalline state and were (ii) measured in an argon atmosphere. The measurements at a low temperature (77K) were made with use of a quartz Dewar while the quartz cell kept cooled with liquid nitrogen. All emission spectra were corrected by use of a standard illuminant. The measurements used, as excitation light, light having a wavelength of 420 nm or 450 nm. The measurements calculated inner quantum yields with use of a solid quantum efficiency calculating program (available from JASCO Corporation). Further measurements were made of the maximum wavelength of light emitted by each light-emitting organic platinum complex.

The measurements produced the results shown in Tables 1 and 2.

TABLE 1

| | Solid light-emission quantum yield φ (%) | | Maximum wavelength of light emission (nm) | |
|---|---|---|---|---|
| Example | 296K | 77K | 296K | 77K |
| 1 | 16.2 | 48.4 | 528 | 516 |
| | | | | 558 |
| 2 | NT | 46.1 | NT | 543 |
| 3 | NT | 19.1 | NT | 554 |
| 4 | NT | 28.1 | NT | 538 |
| | | | | 565 |

TABLE 1-continued

| Example | Solid light-emission quantum yield φ (%) | | Maximum wavelength of light emission (nm) | |
|---|---|---|---|---|
| | 296K | 77K | 296K | 77K |
| 5 | NT | 42.7 | NT | 531 |
| | | | | 576 |
| 6 | 4.7 | 31.2 | 560 | 527 |
| | | | | 569 |
| 7 | 29.8 | 41.9 | 544 | 543 |
| | | | 569 | 567 |
| 8 | 10.4 | 36.7 | 598 | 558 |
| | | | | 603 |
| 9 | 4.1 | 27.2 | 574 | 564 |
| | | | 602 | 609 |
| 10 | NT | 30.0 | NT | 575 |
| 11 | NT | 10.9 | 640 | 609 |
| 12 | NT | 19.2 | NT | 541 |
| | | | | 582 |
| 13 | NT | 60.5 | NT | 514 |
| | | | | 544 |
| 14 | NT | 70.5 | NT | 530 |
| | | | | 566 |
| 15 | NT | 49.4 | NT | 542 |
| | | | | 572 |
| 16 | 19.7 | 47.7 | 568 | 540 |
| | | | | 583 |

*NT stands for "Not tested".

TABLE 2

| Example | Solid light-emission quantum yield φ (%) | | Maximum wavelength of light emission (nm) | |
|---|---|---|---|---|
| | 296K | 77K | 296K | 77K |
| 17 | 6.6 | 29.8 | 608 | 570 |
| | | | | 621 |
| 18 | 17.2 | 67.2 | 599 | 559 |
| | | | | 603 |
| 19 | NT | 6.5 | NT | 624 |
| | | | | 514 |
| 20 | 18.3 | 66.7 | 553 | 551 |
| 21 | NT | 12.8 | NT | 520 |
| | | | | 560 |
| 22 | NT | 10.9 | NT | 586 |
| | | | | 663 |
| 23 | 28.2 | 56.4 | 579 | 544 |
| 24 | 4.8 | 12.9 | 587 | 561 |
| 25 | 38.0 | 50.2 | 581 | 539 |
| | | | | 562 |
| 26 | NT | 27.0 | NT | 611 |
| 27 | NT | 65.9 | NT | 522 |
| | | | | 547 |
| 28 | 36.9 | 40.1 | 567 | 524 |
| | | | | 564 |
| 29 | 9.7 | 59.6 | 550 | 548 |
| | | | 577 | 595 |
| 30 | 3.4 | 21.6 | 594 | 559 |
| | | | | 603 |
| 31 | 36.5 | 69.4 | 576 | 538 |
| | | | | 581 |
| 32 | 11.2 | 63.7 | 551 | 525 |
| | | | | 563 |

*NT stands for "Not tested".

The present invention is not limited to the description of the embodiments above, but may be altered in various ways by a skilled person within the scope of the claims. Any embodiment based on a proper combination of technical means disclosed in different embodiments is also encompassed in the technical scope of the present invention.

INDUSTRIAL APPLICABILITY

The light-emitting organic platinum complex of the present invention, the light-emitting material containing this complex, and the functional device containing this complex are each (i) superior in luminous efficiency to conventional organometallic complexes and (ii) able to achieve emission intensity sufficient for practical use and produce all the three primary colors of light. The present invention can thus advantageously provide (i) a light-emitting organic platinum complex useful as a material for a functional device such as an organic light-emitting element, (ii) a light-emitting material containing the light-emitting organic platinum complex, and (iii) a functional device containing the light-emitting organic platinum complex.

The light-emitting organic platinum complex of the present invention, the light-emitting material containing this complex, and the functional device containing this complex are thus each (i) promising as a material for a functional device such as an organic light-emitting element, which represents a next-generation technique, specifically, promising as a material for, for example, an organic EL (electroluminescence) display or a white LED (light-emitting diode), which is a next-generation lighting device, and (ii) widely usable in various industries.

The invention claimed is:

1. A light-emitting organic platinum complex represented by any one of structural formulae below:

[Chem.1]

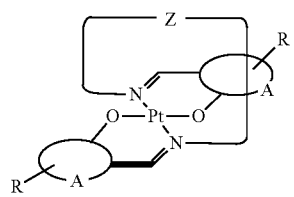

(1)

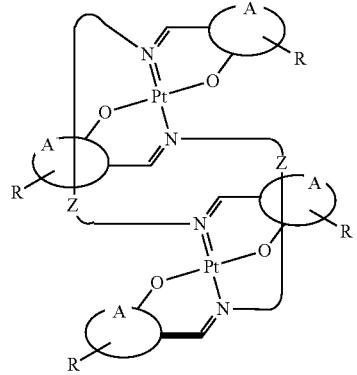

(2a)

-continued (2b)

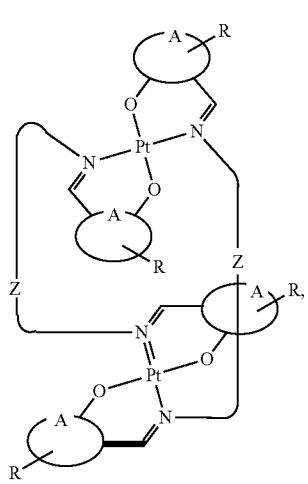

wherein for structural formula (1):

Z is —CH$_2$(CH$_2$OCH$_2$)$_m$CH$_2$—;

m represents 3 or 4;

A is a benzene ring; and

R is hydrogen, a halogen, a methyl group, an ethyl group, a methoxy group, an ethoxy group, a trifluoromethoxy group, a difluoromethoxy group, a hydroxy group, a hydroxyethyl group, a dimethylamino group, a diethylamino group, a nitro group, an acetoxy group, a phenyl group, an alkyl phenyl oxy group having 7 to 13 carbon atoms, an alkynyl phenyl group having 8 to 13 carbon atoms, or an alkenyl phenyl group having 8 to 13 carbon atoms;

wherein structural formula (2a) or (2b) is either:

Z is —(CH$_2$)$_n$—;

n is an integer of 7 to 14;

A is a benzene ring; and

R is hydrogen, a halogen, a methyl group, an ethyl group, a methoxy group, an ethoxy group, a trifluoromethoxy group, a difluoromethoxy group, a hydroxy group, a hydroxyethyl group, a dimethylamino group, a diethylamino group, a nitro group, an acetoxy group, a phenyl group, an alkyl phenyl oxy group having 7 to 13 carbon atoms, an alkynyl phenyl group having 8 to 13 carbon atoms, or an alkenyl phenyl group having 8 to 13 carbon atoms;

or

Z is —CH$_2$(CH$_2$OCH$_2$)$_m$CH$_2$—;

m represents 3 or 4;

A is a benzene ring; and

R is hydrogen, a halogen, a methyl group, an ethyl group, a methoxy group, an ethoxy group, a trifluoromethoxy group, a difluoromethoxy group, a hydroxy group, a hydroxyethyl group, a dimethylamino group, a diethylamino group, a nitro group, an acetoxy group, a phenyl group, an alkyl phenyl oxy group having 7 to 13 carbon atoms, an alkynyl phenyl group having 8 to 13 carbon atoms, or an alkenyl phenyl group having 8 to 13 carbon atoms.

2. A light-emitting organic platinum complex represented by any one of structural formulae below:

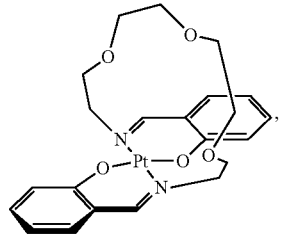
(x)

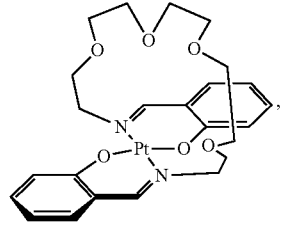
(y)

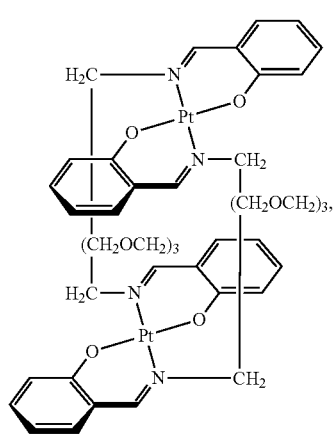
(ab)

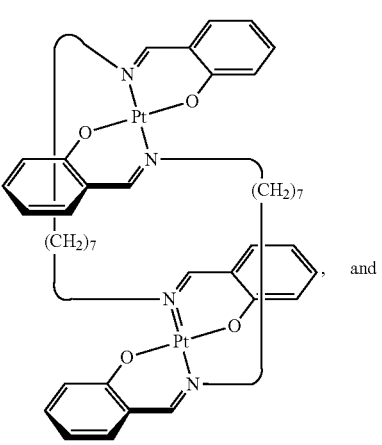
(af)

, and

-continued

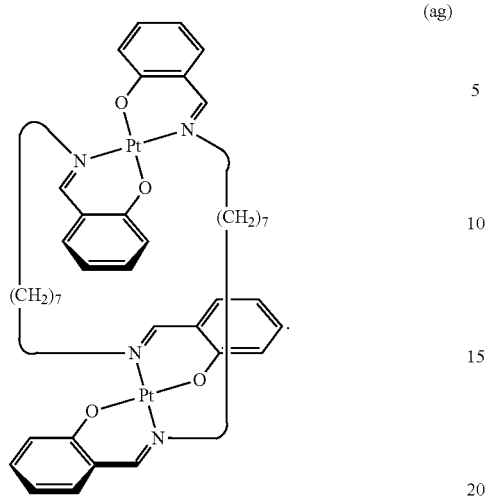

(ag)

3. A light-emitting material comprising:
the light-emitting organic platinum complex according to any one of claim 1 or 2.

4. A functional device comprising:
a pair of electrodes; and
an organic layer sandwiched between the pair of electrodes, the organic layer including a light-emitting layer, the light-emitting layer including the light-emitting organic platinum complex according to any one of claim 1 or 2.

* * * * *